United States Patent [19]

Dunbar et al.

[11] Patent Number: 5,175,166
[45] Date of Patent: Dec. 29, 1992

[54] MUSCARINIC AGONISTS

[75] Inventors: Philip G. Dunbar; Graham J. Durant; Wayne P. Hoss; William S. Messer, Jr, all of Toledo, Ohio

[73] Assignee: The University of Toledo, Toledo, Ohio

[21] Appl. No.: 750,504

[22] Filed: Aug. 27, 1991

[51] Int. Cl.$^5$ ............... A61K 31/44; A61K 31/505; C07D 239/02; C07D 211/72

[52] U.S. Cl. ....................... 514/275; 514/256; 514/269; 514/272; 514/549; 514/352; 514/356; 544/298; 544/332; 544/335; 546/290; 546/297; 546/309; 546/310

[58] Field of Search ............ 544/298, 331, 332, 333, 544/335; 546/268, 277, 280, 304, 309, 310, 311, 312, 290, 297; 514/256, 269, 340, 342, 336, 349, 352, 354, 356, 357, 272

[56] References Cited

U.S. PATENT DOCUMENTS 4,710,508 12/1987 Bergmeier et al. ............... 514/357
4,786,648 11/1988 Bergmeier et al. ............... 514/357

FOREIGN PATENT DOCUMENTS 0259621 3/1988 European Pat. Off.
0296721 12/1988 European Pat. Off.
0384288 8/1990 European Pat. Off.

OTHER PUBLICATIONS

STN international Registry No. 99767-88-1, p. 22, 1898 American Chemical Society Chem Abstracts, vol. 53, 5276E Yakugaku Zasshi, 78, 1166-70 (1958).
Proceedings of the British Pharmacological Society, 2nd-4th Apr., 1970 pp. 191-192.
Chem Abstract Registration No. 117305-84-7.
Chem Abstract Registration No. 96702-03-3.
Chem Abstract Registration No. 103(1):3305J.
Chem Abstract Registration No. 13519-32-9.
Chem Abstract Registration No. 823-05-2.
Chem Abstract Registration No. 13519-33-0.
"Synthesis & Biological Activity of 1,2,4-Oxadiazole Derivatives: Highly Potent & Efficacious Agonists for Cortical Muscarinic Receptors", J. Med, Chem. 1990, 33, 2690-2697.
"Tetrahydropyridyloxadiazoles: Semirigid Muscarinic Ligands", J. Med., Chem. 1991, 34, 1086-1094.
"The Synthesis & Pharamacology of Some 1,4,5,6-Tetrahydropyrimidines", Br. J. Pharmac. (1969), 37, 425-435.
"Synthesis", Jul. 1975, pp. 426-427.
Chem Abstracts 89, 1978, No. 89:109351d (Structure I) & 83, 1975, Abstract 178745y.
"Routes to Functionalized Guanidines. The Synthesis of Guanidino Diesters", J. Org. Chem., vol. 38, No. 8, 1973.
"Novel Quinuclidine-Based Ligands for the Muscarinic Cholinergic Receptor", J. MEd. Chem. 1990, 33, 1128-1138.
"Muscarinic Cholinergic Agonists & Antagonists of the 3-(3-Alkyl-1,2,4-oxadiazol-5-yl)-1,2,5,6-tetrahydropyridine Type, Synthesis & Structure-Activity Relationships", J. Med. Chem. 1991, 34, 687-692 by Sauerbert, et al.
J. Med. Chem. 1990, 33, 2052-2059, colum 1, p. 2052 & column 2 p. 2053.
European Journal of Pharmacology, 134 (1987) 61-67, "Stimulation of Ganglionic Muscarinic $M_1$ Receptors by a Series of Tertiary Arecaidine & Isoarecaidine Esters in the Pithed Rat", p. 62.

Primary Examiner—Cecilia Tsang
Attorney, Agent, or Firm—Marshall & Melhorn

[57] ABSTRACT

Substituted 1,4,5,6-tetrahydropyrimidine compositions, substituted 1,2,3,6-tetrahydropyrimidine compositions and substituted 3,4,5,6-tetrahydropyridine compositions are disclosed. They are useful for stimulating muscarinic receptors including, for example, treating the symptoms of cognitive disorders, especially impared memory, which are associated with decreased acetylcholine synthesis and cholinergic cell degeneration.

46 Claims, No Drawings

MUSCARINIC AGONISTS

TECHNICAL FIELD

This invention relates to drugs and more specifically the invention relates to heterocyclic drug compositions containing carbon and nitrogen atoms in the ring. Even yet more specifically the present invention relates to substituted 1,4,5,6-tetrahydropyrimidine compositions, substituted 1,2,3,6-tetrahydropyrimidine compositions, and substituted 3,4,5,6-tetrahydropyridine compositions.

The invention also relates to treating mammals with such compositions. Further, the invention also relates to pharmaceutical preparations comprising such compositions and a suitable carrier.

BACKGROUND ART

The neurotransmitter acetylcholine mediates a variety of responses within the central nervous system and plays an important role in memory function and cognition. Cholinergic responses are mediated by muscarinic and nicotinic receptors throughout the brain, although it is accepted generally that receptors in the cerebral cortex and hippocampus are associated with memory and cognitive function. Agents that block acetylcholine activity at muscarinic receptors and lesions of cholinergic projections to the cortex and hippocampus impair memory and cognition.

In humans, the nucleus basalis of Meynert is the source of acetylcholine for the cerebral cortex and hippocampus. The cholinergic cells within the basal nucleus degenerate in Alzheimer's disease, a disorder that is associated with memory dysfunction and progressive cognitive decline. Current therapeutic approaches for Alzheimer's disease include treatment with agents that increase levels of acetylcholine or mimic the effects of acetylcholine at receptors.

Efforts to increase acetylcholine levels have focused on increasing levels of choline, the precursor for acetylcholine synthesis, and on blocking acetylcholinesterase (AChEase), the enzyme that metabolizes acetylcholine. The first approach, using either choline or phosphatidylcholine, has not been very successful although acetylcholinesterase inhibitors have shown some therapeutic efficacy. Clinical trials with these compounds have documented some improvements in cognitive function and ability to conduct daily tasks. Major drawbacks with AChEase inhibitors include toxicity and the side effects associated with activation of receptors in the peripheral nervous system.

Recent efforts have focused on treating Alzheimer's patients with agonists for muscarinic cholinergic receptors. Natural products, such as the arecoline and pilocarpine ligands, can mimic the effects of acetylcholine at receptors in the central nervous system and reverse cognitive impairments in experimental animals. The clinical application of such ligands is hampered however by the low intrinsic activity of these compounds and their rapid metabolism. Other muscarinic agonists with higher efficacy are not suitable due to either low bioavailability or profound side effects associated with peripheral activity.

Recent molecular biological studies have cloned five subtypes of muscarinic receptors, each with a unique amino acid sequence, tissue-specific expression, ligand binding profile and associated biochemical response. Each subtype is expressed within the central nervous system, although m1, m3 and m4 receptors predominate in the cerebral cortex and hippocampus. In peripheral tissues, the heart expresses m2 receptors while m3 receptors are found in exocrine glands. Pirenzepine, AF-DX 116 and p-F-hexahydrosiladifenidol are selective antagonists for $M_1$, $M_2$ and $M_3$ receptors respectively. Three subtypes (m1, m3 and m5) couple selectively to the stimulation of phosphoinositide metabolism while m2 and m4 more efficiently inhibit adenylyl cyclase.

In addition to the recent studies showing the preferential localization of $M_1$ receptors in the cerebral cortex and hippocampus, recent findings also show that $M_1$ antagonists, such as pirenzepine, produce memory impairments in experimental animals.

Thus, it will be appreciated by those skilled in the art that what is needed in the art to reverse the cognitive and memory deficits associated with a loss of cholinergic neurons, as found in Alzheimer's disease, is a selective muscarinic agonist with high central nervous system activity. This agonist should bind selectively to $M_1$ muscarinic receptors, localized predominantly in the cerebral cortex and hippocampus. It should stimulate phosphoinositide metabolism in the hippocampus.

Even more broadly, however, there is a need in the art to provide muscarinic agonists which have activity at various muscarinic receptor subtypes in the central and peripheral nervous system.

DISCLOSURE OF THE INVENTION

It is an object of this invention to satisfy the above described needs in the art. In accordance with one aspect this invention an $M_1$ selective muscarinic agonist with high central nervous system activity is provided. In accordance with a broader aspect, therapeutic benefits are provided by providing improved compositions which stimulate muscarinic receptors.

The object of this invention is accomplished by providing compounds having the formula (i), (ii) or (iii) set forth below or a pharmaceutically acceptable salt thereof:

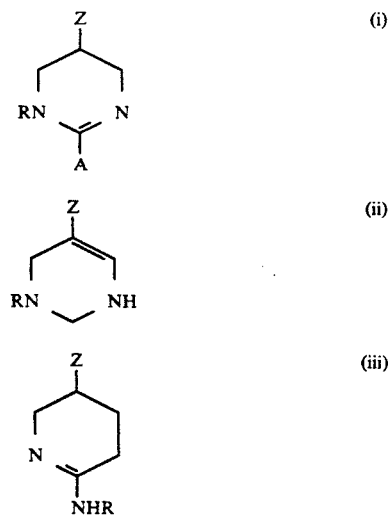

In the above: A is H or NHR; R is H, an alkyl of 1-8 carbon atoms, preferably 1-4, and most desirably, 1-3 carbon atoms, —C(O)—$R^1$ or —C(O)O$R^1$; Z is —C(O)O$R^1$, or —OC(O)$R^1$, or

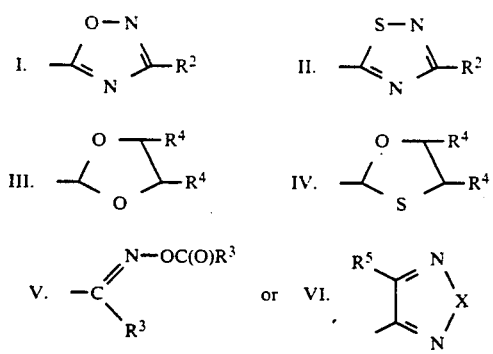

wherein X is O or S, and wherein $R^1$ is a monovalent hydrocarbon radical having 1-8 carbon atoms, preferably 1-4, and most desirably, 1-3 carbon atoms, $R_2$ is alkyl of 1-8 carbon atoms, preferably 1-4, and most desirably, 1-3 carbon atoms, alkylthioalkyl of up to 8, preferably up to 3 or 4, carbon atoms, alkoxyalkyl of up to 8, preferably up to 3 or 4, carbon atoms or NHR, $R^3$ is H or —$CH_3$, $R_4$ is H or an alkyl of 1-8 carbon atoms and wherein $R^5$ is H, an alkyl of 1-8 carbon atoms, alkoxy of 1-8 carbon atoms or an alkylthio group of 1-8 carbon atoms. Suitably, $R^4$ and $R^5$ will contain 1-4 carbon atoms, preferably 1-3. The monovalent hydrocarbon radical may, for example, be an alkyl, an alkaryl, an aryl, an aralkyl, an alkenyl or alkynyl radical.

Exemplary of highly desirable inventive compounds, and their pharmaceutically acceptable salts are: 5-methoxycarbonyl-1,4,5,6-tetrahydropyrimidine; -acetoxy-1,4,5,6-tetrahydropyrimidine; 1-methyl-5-methoxycarbonyl-1,2,3,6-tetrahydropyrimidine; 2-amino-5-methoxycarbonyl-3,4,5,6-tetrahydropyridine; 5-ethoxycarbonyl-1,4,5,6-tetrahydropyrimidine; propynyl 1,4,5,6-tetrahydropyrimidine-5-carboxylate; 5(3-methyl-1,2,4-oxadiazol-5-yl)-1,4,5,6 tetrahydropyrimidine. Also highly desirable are those compounds where Z is moiety I, II, III, IV, and VI, especially I, for example, with structure (i) as a nucleus.

In another aspect, the present invention provides an improvement in methods for providing a therapeutic benefit to mammals, for example, those having a cholinergic deficit comprising administering to such mammal, in any convenient manner, a non-toxic amount, but an amount effective to stimulate muscarinic receptors, of a compound as described above, or a pharmaceutically acceptable salt thereof.

In yet another aspect of this invention, pharmaceutical preparations are provided which include amounts effective to stimulate cognitive function of a compound as described above, or pharmaceutically acceptable salt thereof, along with a pharmaceutically acceptable solid or liquid carrier.

It will, of course, be apparent to those skilled in the art that when reference is made to the compounds, or salts, of this invention, such terminology includes within its scope the various forms of such compounds, and salts. Thus such terminology includes the various stereoisomers and, for example, various tautomeric forms. It also includes forms which when administered into the body form such compositions.

DETAILED DESCRIPTION INCLUDING THE BEST MODE OF CARRYING OUT THE INVENTION

Theraputic Use

It will be apparent that the use of the compounds in accordance with this invention, by virtue of the basic nitrogen in the tetrahydropyridine and the tetrahydropyrimidine rings may be employed in the form of their pharmaceutically acceptable salts. The salts will be formed in a known conventional manner and the preferred salts are organic acid or an inorganic acid addition salts. Examples of suitable acids for the formation of pharmaceutically acceptable acid addition salts are hydrochloric, sulfuric, phosphoric, acetic, trifluoro acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane and hydroxyethanesulfonic acids and the like. Further particulars can be had by reference to the Journal of Pharmaceutical Science, 66 (1) 1-19 (1977).

In the discussion which follows, including the examples and claims, unless otherwise expressly indicated, when reference is made to any compound of the present invention, the term compound includes, therefore, any pharmaceutically acceptable salt thereof and forms which release substantially the same active moiety as said compound or salt.

In therapeutic uses as agents for treating cholinergic insufficiency, the compounds utilized in the pharmaceutical method of this invention are desirably administered to the patient in amounts effective to stimulate muscarinic receptors and thereby stimulate central and/or peripheral nervous systems. Since the compounds of this invention will stimulate central muscarinic acetylcholine receptors they are useful when administered in effective amounts, to treat not only presenile and senile dementia but also Huntington's chorea, tardive dyskinesia, hyperkinesia, mania and Tourette syndrome. In effective amounts, they are also useful as analgesics, for example, in treating painful conditions like rheumatism, arthritis and terminal illness and they are useful in the peripheral nervous system to treat glaucoma and atonic bladder conditions. The effective amounts vary but usually translate to dosage levels of from about 0.7 to about 7000 mg per day. For a normal human adult of approximately 70 kg of body weight this translates into a dosage of about from 0.01 to 100 mg/kg of body weight per day. The specific dosages employed, however, may vary depending upon the requirements of the patient, the severity of the condition being treated and the activity of the compound being employed. The determination, however, of optimum dosages for any particular situation is well within the skill of the art.

In preparing pharmaceutical compositions of the compounds (or their pharmaceutically acceptable salts) of this invention, inert, solid or liquid pharmaceutically acceptable carriers will be employed. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to comprehend within its scope a formulation of the active compound with encapsulating material as a carrier, thereby providing a capsule in which the active component (with or without other carriers) is surrounded by a carrier and is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol are mentioned as examples of liquid preparations suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, or other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself.

Representative Compounds of the Invention, Their Synthesis and Properties

Representative of the alkyl, alkoxy and alkylthio groups from which the various R substituents on structures (i), (ii) and (iii) will be selected in forming compounds of the present invention are methyl, ethyl, propyl, butyl and its various isomers, methoxy, ethoxy, propoxy, hexoxy as well as, for example, methyl, ethyl and propylthio groups. Representative of the aryl, alkaryl, aralkyl, alkenyl and alkynyl groups from which $R^1$ may be selected on those structures are phenyl (aryl), methylphenyl (alkaryl), phenylmethyl (aralkyl), ethenyl and propenyl (alkenyl) as well as ethynyl and propynyl, i.e. propargyl (alkynyl). Representative of alkylthioalkyl radicals are methylthioethyl and ethylthiopropyl whereas methoxypropyl and ethoxymethyl are representative of alkoxyalkyl radicals. Equivalent moieties, for example, those presenting no steric hindrance complications, will be selected by those skilled in the art. It is preferred that the $R^1$ hydrocarbon radical be an alkyl radical of one or two carbon atoms. Preferably the hydrocarbon radical will not be propyl, isopropyl or benzyl.

Representative of the muscarinic agonist having high central nervous system activity as contemplated by the present invention and which will selectively bind to $M_1$ muscarinic receptors and stimulate phosophoinositide metabolism in the brain are those of the above with the following structures: (ii) and wherein R is $CH_3$ and Z is $C(O)OCH_3$, that is, 1-methyl-5-methoxycarbonyl-1,2,3,6-tetrahydropyrimidine; (i) wherein R is H, Z is $OC(O)CH_3$ and wherein A is H, that is, 5-acetoxy-1,4,5,6-tetrahydropyrimidine; (iii) wherein R is H and wherein D at the 5 position is $C(O)OCH_3$ and wherein D at the 6 position is H, that is, 2-amino-5-methoxycarbonyl-3,4,5,6-tetrahydropyridine; (i) wherein A is H, R is H and Z is $—C(O)OCH_3$, that is, 5-methoxycarbonyl-1,4,5,6-tetrahydropyrimidine; (i) wherein Z is $—C(O)OC_2H_5$, A is H and R is H, that is, 5-ethoxycarbonyl-1,4,5,6-tetrahydropyrimidine; (i) wherein Z is moiety VI and X is S and $R^5$ is alkoxy and A is H and R is H; (i) wherein Z is I, $R^2$ is methyl and A is H and R is H; (i) wherein Z is gamma-propynyloxycarbonyl and R and A are H.

Compounds of the present invention are prepared by the schematically depicted chemical reaction sequences (I–XXXVII) below.

Schematic sequence I (a) and (b) illustrate the production of compounds of structures (i) and (iii) above. In this reaction sequence, a properly substituted pyridine or pyrimidine is catalytically reduced to the tetrahydro derivative and then alkylated to those structures. Starting with a pyrimidine reactant, compounds of structure (ii) are produced by the schematic sequence II (a) and (b). This sequence first involves an alkylation to produce a quaternary compound which then is subjected to a sodium borohydride reduction to produce a desired structure.

In this description of the reaction sequences, the term alkylation (or dealkylation), for simplicity, is used not only to refer to the introduction (or removal) of an alkyl radical into a molecule but also the introduction (and removal) of other monovalent hydrocarbon radicals, e.g. alkaryl, aryl, araalkyl, alkenyl etc., into a molecule.

Compounds of structure (i) and (iii) or compounds of structure (ii) can respectively be produced in accordance with reaction sequences III and IV respectively by starting with a properly substituted acyl pyridine or acyl pyrimidine. According to reaction sequence III (a) and (b), the acyl pyridine or pyrimidine in reaction sequence III (a) will be catalytically reduced to form the tetrahydro derivative. This tetrahydro derivative will be alkylated (III b) followed by reaction with an acyl oxamine to thereby form the acyl oxime. In accordance with reaction sequence IV (a) and (b), compounds of structure (ii) will be formed by first of all reacting the substituted pyrimidine with an acyl oxamine followed by alkylation (IV a) to form the quaternary compound which is subjected to sodium borohydride reduction (IV b) to produce structure (ii).

Reaction sequence V a,b,c produces compounds of structure (i) by starting with a hydroxy diamino propane. The hydroxy diamino propane is first subjected to a condensation reaction (V a) with a formate or carbamate and the reaction product is esterified with an organic acid (V b). The 1,4,5,6-tetrahydropyrimidine ester is then subjected to alkylation (V c) to produce compounds (i).

Structures (i) and (iii) are produced by reaction sequences VIII, XII, XIII and XIV. In reaction sequence VIII, a properly substituted bromo pyridine or pyrimidine is subjected to halogen—metal exchange followed by carboxylation and esterification to produce the pyridine or pyrimidine ester. The ester (sequence XII) is then subjected to catalytic reduction followed by alkylation (XIII) to produce a protected tetrahydro ester. Structures (i) and (iii) are produced from that ester by sequence XIV. Sequence XIV shows a procedure, in which a properly substituted amidoxime, or a hydroxy guanidine (or sulphur analogs thereof), is reacted, under basic catalysis (sodium hydride), with the protected tetrahydro ester to produce the (i) or (iii) structures.

Sequence XV shows the deprotection or dealkylation of the products of sequence XIV to produce compound structures (i) when Y is NR', R' is trityl or C(O)OR (with R being a monovalent hydrocarbon of 1–7 carbon atoms) in such products.

Chemical structures (i) and (iii) can be formed in accordance with reaction sequence VI and VII. The brominated pyridine or pyrimidine is first subjected to halogen-metal exchange and carboxylation followed by catalytic reduction (VI) to produce the acid. This acid is then esterified (VII) in the presence of thionylchloride and then alkylated to produce compounds (i) and (iii).

Structure (ii) can be produced by reaction sequences VIII, IX and X. As previously described, reaction sequence VIII is used to form the pyridine or pyrimidine ester. This ester is then subjected to alkylation (IX) to form a quaternary compound and this quaternary compound is then reduced (X) to compounds of structure (ii).

Steps VIII, XI and XVII can also be employed to produce compounds of structure (ii). The pyrimidine ester of step VIII is, under basic catalysis (NaH), reacted with a properly substituted amidoxime or hydroxyguanidine (or sulphur analog thereof), as indicated in step XI, to form a pyrimidine having oxadiazole or thiadiazole substitution. That substituted pyrimidine is then (step XVII) subjected to quaternization and borohydride reduction to produce compounds of structure (ii).

Compounds of structure (ii) can also be formed in accordance with reaction sequence XVI and XVII. In this sequence, a pyrimidine thioamide is subjected to condensation with a substituted ortho amide and then cyclized by amination with, for example, hydroxylamine-O sulfonic acid (step XVI). This is followed in turn by step XVII as described above.

Compounds of structure (ii) can be formed by reaction sequence XXXIV and compounds (i) and (iii) can be formed by reaction sequences XXXV and XXXVI. In reaction sequence XXXIV, pyrimidine aldehydes are converted to oxathiolanes or dioxolanes by a process which involves dehydration using a properly substituted glycol or a thiol followed by quaternization and then sodium borohydride reduction. Compounds (i) or (iii) are sequentially produced (step XXXV) by catalytic reduction of the pyridine or pyrimidine aldehyde and alkylation to produce the 3,4,5,6-tetrahydropyridine or the 1,4,5,6-tetrahydropyrimidine structure. The tetrahydropyridine or the tetrahydropyrimidine compositions are then subjected to dehydration with a properly substituted glycol or thiol (step XXXVI) to produce compounds (i) and (iii).

Compounds (i) and (iii) can also be produced by the reaction sequence of steps XIX, XXI, and XXIV and compounds of structure (i) can also be produced by sequence XIX, XX, XXII and XXV. Compounds of structure (ii) can be produced by reaction sequence XIX, XXI and XXIII. The initial reaction in forming these compounds is a Strecker synthesis (XIX) to form the amino nitrile intermediate. In sequence XXI, the amino nitrile compound is subjected to cyclization using sulfur monochloride to produce a halo thiadiazole alkylating agent. In sequence XXIII, this alkylating agent is then reacted with a metal alkyl, or with a compound having an alkoxy or alkylthio anion, followed by quaternization and sodium borohydride reduction to produce a thiadiazole of structure (ii). In accordance with sequence XXIV, the halo thiadiazole alkylating agent of step XXI is reacted (step XXIV) with a metal alkyl, or, for example, with an alkoxy or alkylthio anion followed by catalytic reduction and, alkylation to form thiadiazole compounds of structure (i) and (iii).

Compounds (i) and (iii) of sequence XXIV can also be converted to (i) structures, when Y is NR', R' is C(O)R or trityl, by deprotection with TFA (trifluoroacetic acid).

As indicated above, the aminonitrile compound resulting from the Strecker synthesis (sequence XIX) can also be formed into compound (i) by reaction sequences XX, XXII and XXV. In sequence XX the aminonitrile is hydrolized, with the product then being subjected to catalytic reduction and alkylation to produce a protected pyrimidine amide. This protected pyrimidine is then subjected to cyclization (XXII) employing sulfur monochloride, or thionylaniline, to produce a hydroxy thiadiazole substituent on a 1,4,5,6-tetrahydropyrimidine nucleus. Finally, compounds of formula (i) are formed when R' is C(O)OR or trityl in the product of step XXII in accordance with step XXV by alkylation and deprotection.

Using a cyano methyl pyrimidine compound, compounds of structure (ii) can be formed by reaction sequences XXVII, XXVIII and XXX. From a properly substituted cyano methyl pyridine or pyrimidine compound, structures (i) and (iii) can be formed by reaction sequences XXVII, XXVIII and XXXI. Compounds of structure (i) can also be formed by reaction sequence XXVII, XXXVII, XXIX and XXXII.

In reaction sequence XXVII, the substituted pyridine or pyrimidine compound is subjected to a base catalyzed reaction with a methylnitrite to form a cyano oxime. The cyano oxime is then reacted (sequence XXVIII) with hydroxylamine and then cyclized using phosphorous pentachloride and the cyclized product is then subjected to diazotization and then chlorination to produce an alkylating halooxadiazole substituted halo pyridine or pyrimidine compound. In reaction sequence XXX, the pyrimidine compound is reacted with a metal alkyl or with an MX'R compound and then subjected to quaternization followed by sodium borohydride reduction to produce compounds of structure (ii).

The step XXVIII compound is used to form compounds of structure (i) or (iii) in accordance with reaction sequence XXXI by first of all reacting with an R" M compound followed by catalytic reduction and then alkylation when Y is N. It can be observed in the reaction sequences that by dealkylation, or deprotection, compounds produced in accordance with reaction sequence XXXI, when Y is NR' and R' is C(O)OR or trityl, can be converted to compounds of structure (i) as illustrated in reaction sequence XXXIII.

The cyano oxime of reaction sequence XXVII can also be converted, through reaction sequences XXXVII, XXIX and XXXII, to compounds of structure (i). In reaction sequence XXXVII, the cyano oxime is reacted with hydroxylamine and then subjected to catalytic reduction followed by alkylation to form the properly protected amino oxime. The latter material, in accordance with reaction sequence XXIX, is subjected to cyclization, using phosphorous pentachloride, and then subjected to diazotization and chlorination to form an alkylated, chlorooxadiazole substituted, tetrahydropyrimidine structure which is then employed as an alkylating agent in reaction sequence step XXXII to react with an R" M compound followed by deprotection with TFA to produce structure (i).

The symbols used above, e.g. R", M, R, etc., to describe the various reaction sequences are those set forth below in the respective reaction sequence flow diagrams. In the above description, it will be apparent that alkylation, along with protection, is provided when required for the selected properly substituted product.

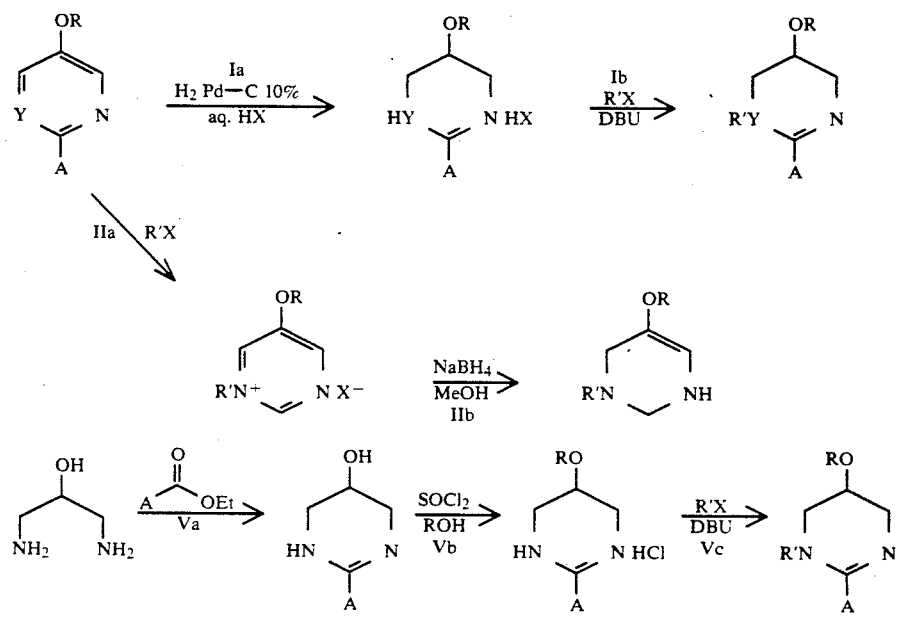

R = Acyl of 1-8 carbons
R' = H, Hydrocarbon of 1-8 carbons, Trityl, C(O)R", C(O)OR"(R" = Hydrocarbon of 1-8 carbons)
A = H, NHR'
Y = N, CH
X = Halogen

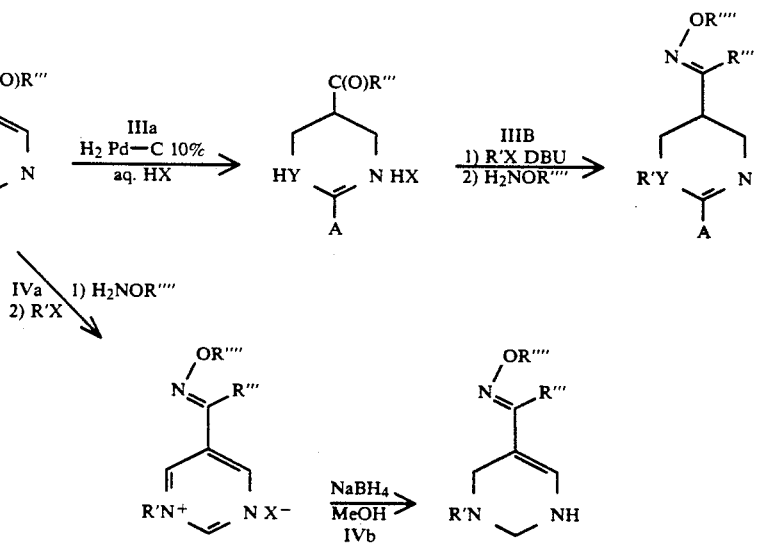

R′=H, Hydrocarbon of 1-8 carbons, Trityl, C(O)R″,
C(O)OR″(R″=Hydrocarbon of 1-8 carbons)
R‴=H, CH₃; R⁗=C(O)CH₃, C(O)H
A=H, NHR′
X=Halogen
Y=N, CH
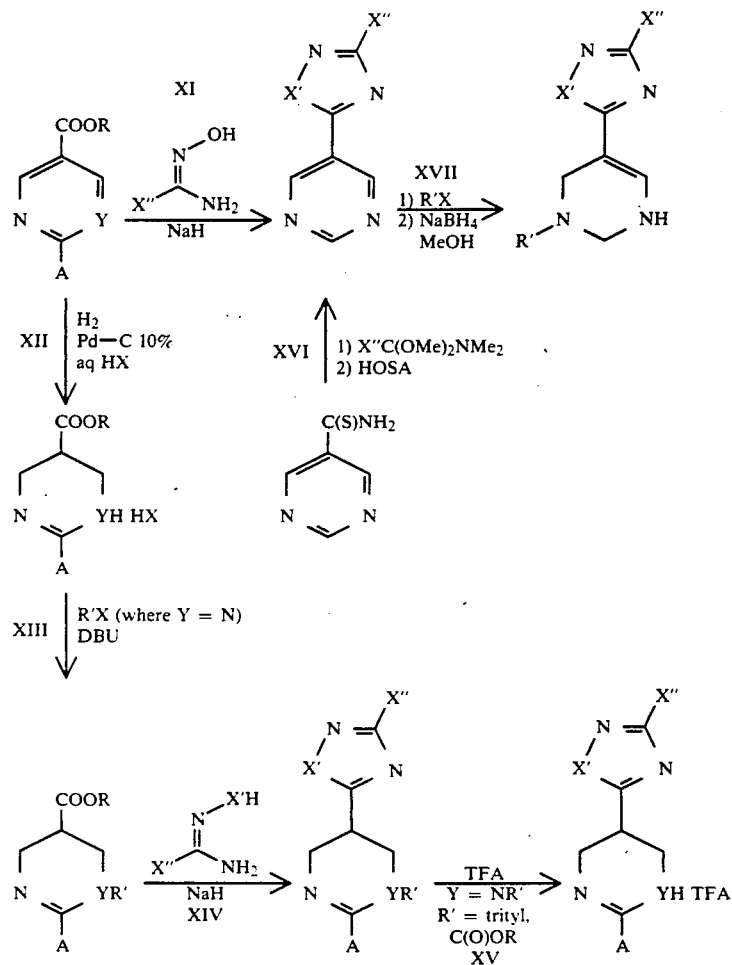
A=H, NHR′
Y=N, CH
X=Halogen
R=Acyl of 1-8 carbons
R′=H, Hydrocarbon of 1-8 carbons, Trityl, C(O)OR, C(O)R
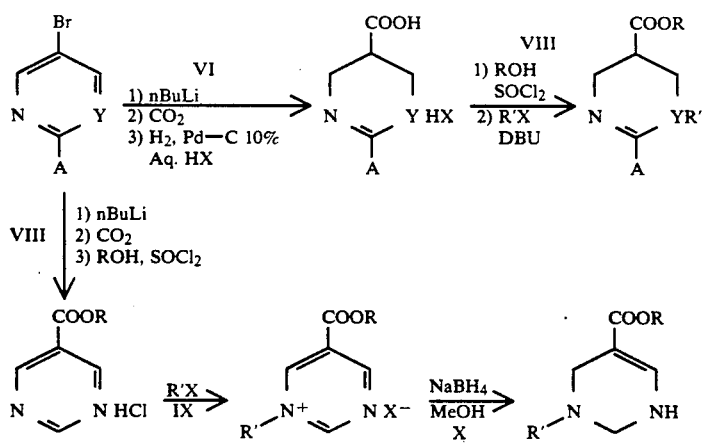
R=Hydrocarbon of 1-8 carbons
R′=H, Hydrocarbon of 1-8 carbons, Trityl, C(O)OR, C(O)R
A=H, NHR′
X=Halogen; X′=S, O; X″=R, (CH₂)ₙX′(CH₂)ₙCH₃(n=1-4), NHR′
Y=N, CH

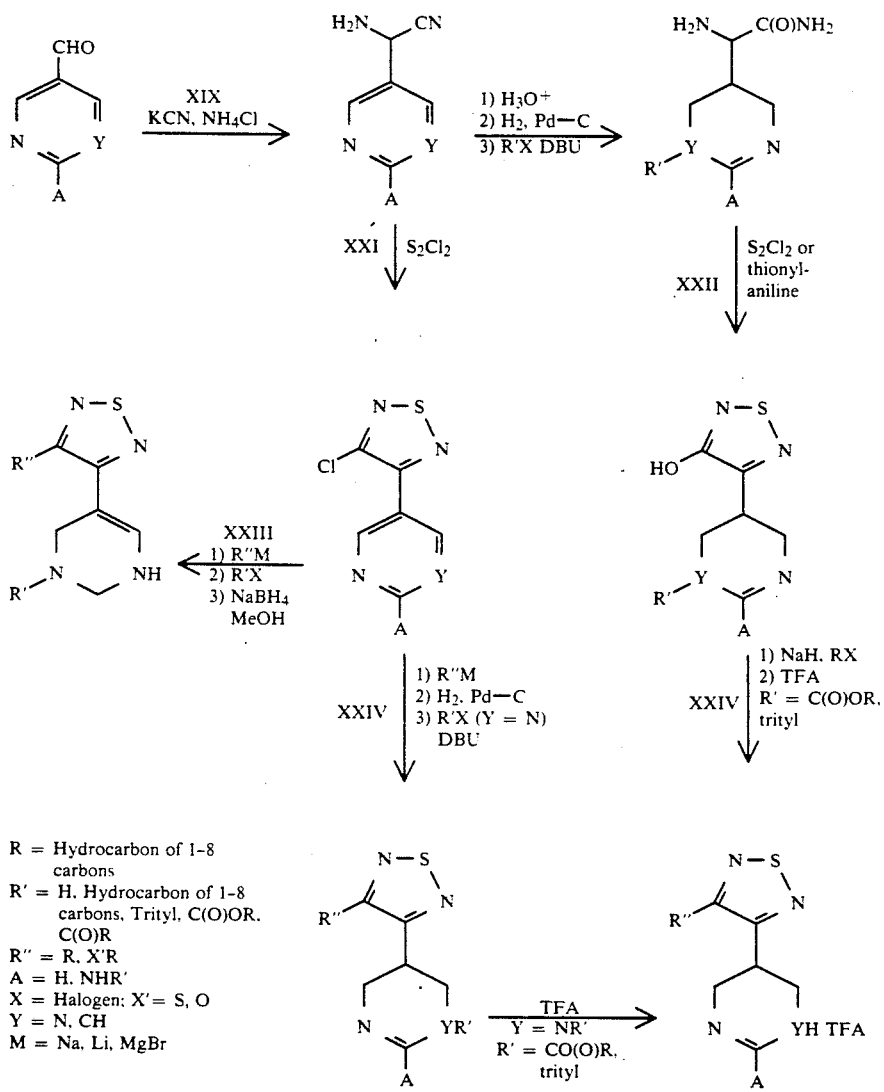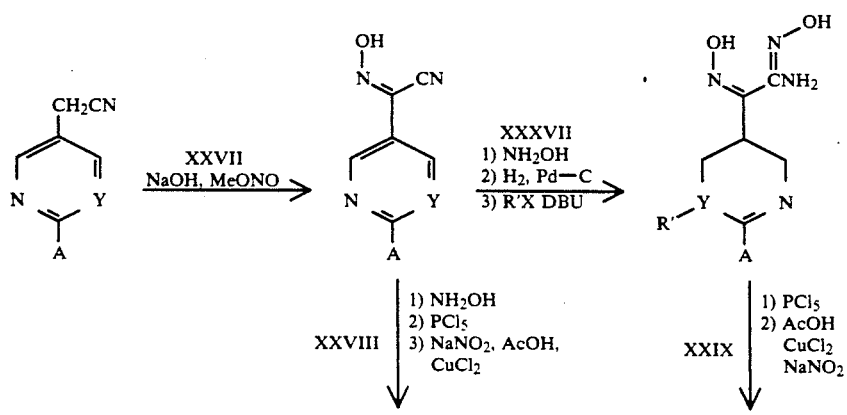

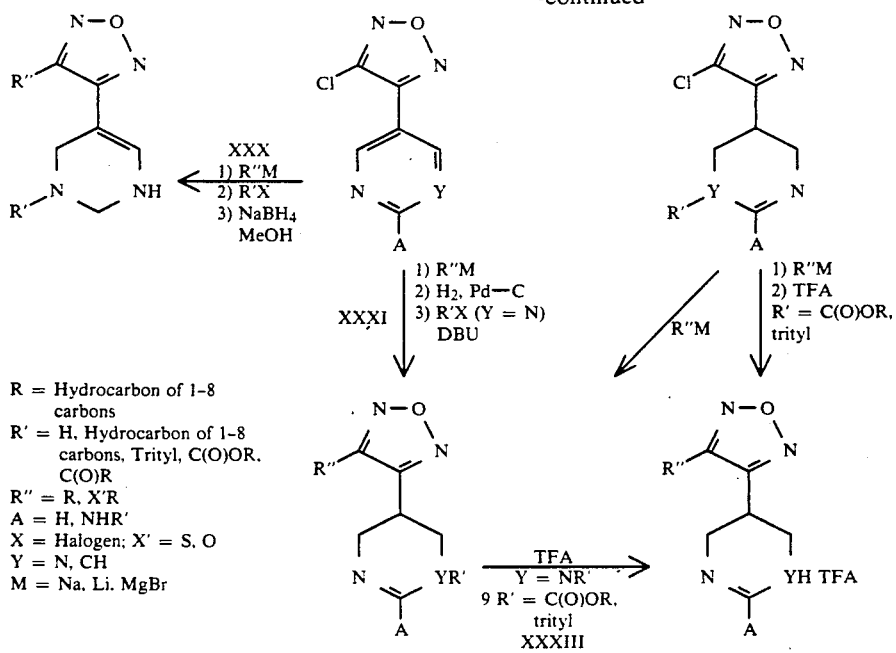

R = Hydrocarbon of 1-8 carbons
R' = H, Hydrocarbon of 1-8 carbons, Trityl, C(O)OR, C(O)R
R" = R, X'R
A = H, NHR'
X = Halogen; X' = S, O
Y = N, CH
M = Na, Li, MgBr

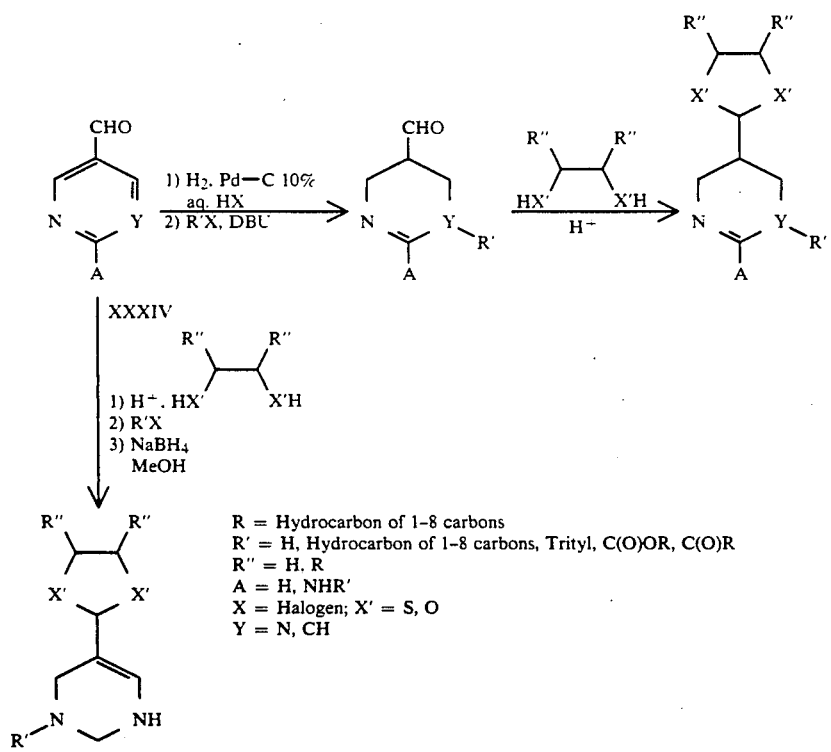

R = Hydrocarbon of 1-8 carbons
R' = H, Hydrocarbon of 1-8 carbons, Trityl, C(O)OR, C(O)R
R" = H, R
A = H, NHR'
X = Halogen; X' = S, O
Y = N, CH Those skilled in the art with the foregoing reaction sequences will routinely select the starting materials needed to produce the compounds, or their pharmaceutically acceptable salts as contemplated by the present invention.

The following preparative examples are further provided to enable and aid those skilled in the art to practice the invention. These examples are representative synthesis techniques, but they are only illustrative of the present invention and are not to be read as limiting the scope of the invention. The examples include not only the general synthesis method for producing compounds, and their pharmaceutically acceptable salts, in accordance with the invention, but also present representative starting material preparation techniques.

EXAMPLES

Example 1

5-Methoxycarbonylpyrimidine

1) Crude pyrimidine-5-carboxylic acid (1.24 g, 10 mmol) was dissolved in 100 ml THF (dry), 3 ml water, and cooled to 0° C. in the reaction vessel of a Mini-Diazald ® apparatus (Aldrich Chemical). Diazald ® (3 g, 14 mmol) dissolved in ether (27.5 ml) was added dropwise over 15 minutes to KOH (3 g) in ethanol/water (11 ml) at 65° C. to generate diazomethane. Ether (20 ml) was added dropwise, after the Diazald ® solution, to co-distill the remaining diazomethane into the reaction flask. The reaction was allowed to stir 3 hours until nitrogen evolution had stopped, and excess diazomethane was then destroyed by adding acetic acid. The solvents were evaporated in vacuo,. the residue taken up in 50 ml water, basified to pH 9 (NaCO₃), and extracted with chloroform (3×100 ml). After drying (MgSO₄), filtering, and evaporating the solvent in vacuo, 1.26 g (91%) crude crystals were obtained. Recrystallization from chloroform/hexane gave 606 mg (44%) light yellow crystals mp 81.6°–86.6° C. Microanalysis calc.: C 52.17, H 4.38, N 20.29; found: C 51.95, H 4.31, N 19.96. 400 MHz nmr indicated product.

2) Crude pyrimidine-5-carboxylic acid (2.4 g, 19.38 mmol) was suspended in 100 ml methanol in a round bottom flask fitted with a reflux condenser, drying tube, and a dropping funnel, and 2.8 ml thionyl chloride was added dropwise with stirring. The suspension was stirred and refluxed overnight; then cooled to room temperature and the solvents evaporated in vacuo. Ice cold water (50 ml) was added, basified to pH 8 (sat. NaHCO₃), and extracted with chloroform (3×50 ml). The organics were dried (MgSO₄), filtered and evaporated in vacuo to yield 2.07 g crude yellow crystals (77%).

1,4,5,6-Tetrahydro-5-methoxycarbonylpyrimidine Hydrobromide

5-Methoxycarbonylpyrimidine (1.381 g, 10 mmol) in 143 ml 0.07158M HBr was hydrogenated at 26 psig over 600 mg Pd-on-carbon 10% in a Parr hydrogenator for three hours. The suspension was filtered and the filter rinsed twice with hot water (10 ml). The filtrate was evaporated in vacuo to give 1.86 g yellow oil (83%). The oil was crystallized from anhydrous ethanol/THF, and the hygroscopic crystals collected by decanting the solvents under a stream of nitrogen. Excess solvents were removed under vacuum in a drying pistol to yield 1.01 g (45%) white crystals mp 149°–153° C. (with the evolution of gas). Microanalysis calc.: C 32.3, H 4.97, N 12.56; found: C 32.12, H 5.15, N 12.34. 400 MHz nmr indicated product.

Example 2

1,4,5,6-Tetrahydropyrimidine-5-carboxylic Acid Hydrochloride

Pyrimidine-5-carboxylic acid (5.0 g, 40 mmol) was suspended in a mixture of 150 ml water and concentrated hydrochloric acid (4.0 g, 40.5 mmol). The mixture was hydrogenated at 26 psig over 1.0 g Pd-on-carbon 10% in a Parr hydrogenator for 3 h. The suspension was filtered and the filter rinsed twice with hot water (20 ml). The filtrate was evaporated in vacuo to give 6.11 g yellow oil (92%). The oil was crystallized from anhydrous methanol/tetrahydrofuran (THF) to give 5.77 g (87%) white crystals in two crops. 300 MHz nmr indicated product.

1,4,5,6-Tetrahydro-5-ethoxycarbonylpyrimidine Hydrochloride 1,4,5,6-Tetrahydropyrimidine-5-carboxylic acid hydrochloride (1.5 g, 9.12 mmol) was dissolved in absolute ethanol (40 ml) by heating. The thionyl chloride (1.1 g, 9.16 mmol) was added dropwise with stirring. The resulting solution was refluxed 20 h and then evaporated to dryness in vacuo. The residue was taken up in absolute methanol (5 ml) and dry THF (10 ml) was added to induce crystallization, giving 1.1 g (63%) product as white crystals, mp 125°–127° C. 300 MHz nmr confirmed the product. Microanalysis calc.: C 43.64, H 6.75, N 14.55; found: C, 43.43, H 6.58, N 14.40.

Example 3 n-Propyl 1,4,5,6-Tetrahydropyrimidine-5-carboxylate Hydrochloride 1,4,5,6-Tetrahydropyrimidine-5-carboxylic acid hydrochloride (1.5 g, 9.1 mmol) was dissolved in 1-propanol (30 ml). To the mixture was added thionyl chloride (1.1 g, 9.1 mmol) and the solution was refluxed for 22 h. The solvent was evaporated in vacuo to dryness. The residue was crystallized from methanol/THF to give 1.06 g (56%) of white crystals, mp 128°–130° C. 300 MHz nmr indicated product. Microanalysis calc.: C 46.49, H 7.26, N 13.56, found: C 46.21, H 6.96, N 17.41.

Example 4

Isopropyl 1,4,5,6-Tetrahydropyrimidine-5-carboxylate Hydrochloride 1,4,5,6-Tetrahydropyrimidine-5-carboxylic acid hydrochloride (1.0 g, 6.08 mmol) was suspended in 2-propanol (50 ml) and thionyl chloride (0.76 g, 6.39 mmol) was added dropwise. The resulting mixture was refluxed 24 h. The pink solution was treated with charcoal and then reduced in volume to 15 ml by evaporating unreacted alcohol. By allowing the solution to stand overnight, white crystals (1.08 g, 84%) were obtained in three crops, mp 170° C. 300 MHz nmr confirmed product. Microanalysis calc.: C 46.49, H 7.26, N 13.56, found: C 46.49, H 7.25, N 13.64.

Example 5

Benzyl 1,4,5,6-Tetrahydropyrimidine-5-carboxylate Hydrochloride 1,4,5,6-Tetrahydropyrimidine-5-carboxylic acid hydrochloride (1.0 g, 6.1 mmol) was suspended in dry benzyl alcohol (20 ml). To the mixture was added thionyl chloride (0.76 g, 6.39 mmol) and the resulting mixture was heated in an oil bath at 80° C. for 24 h. The clear solution was poured to anhydrous ethyl ether (100 ml) to induce precipitation. The white solids were collected and crystallized from methanol/THF to give 1.18 g (76%) of product (mp 113°–114° C.). 300 MHz nmr indicated the product. Microanalysis calc.: C 56.58, H 5.89, N 11.00; found: C 56.34, H 6.03, N 11.19.

Example 6

Propynyl 1,4,5,6-Tetrahydropyrimidine-5-carboxylate Hydrochloride 1,4,5,6-Tetrahydropyrimidine-5-carboxylic acid hydrochloride (2.22 g, 13.5 mmol) was suspended in oxalyl chloride (30 ml). The mixture was refluxed for 6 h with stirring and then unreacted oxalyl chloride was evaporated to dryness. To the residue was added propargyl alcohol (20 ml) and the resulting mixture was stirred for 10 h at room temperature. The mixture was evaporated in vacuo to dryness. The residue was recrystallized from methanol/THF to give white crystals —400 mg (14%), mp 127°–129° C. Microanalysis calc.: C 45.40, H 5.67, N 13.23; found: C 45.55, H 5.70, N 13.18.

Example 7

1,4,5,6-Tetrahydro-5-methoxycarbonylpyrimidine Hydrochloride 1,4,5,6-Tetrahydropyrimidine-5-carboxylic acid hydrochloride (6.34 g, 38.5 mmol) was dissolved in anhydrous methanol (200 ml) with stirring, and thionyl chloride (2.74 ml, 38.5 mmol) was added dropwise. The resulting solution was refluxed with stirring for 18 hours, then evaporated in vacuo to white solids. The crude product was recrystallized from anhydrous methanol to yield 4.12 g (60%) white crystals, mp 160°–164° C. Calculated: C 40.34, H 6.21, N 15.69; found: C 40.17, H 6.41, N 15.73.

1-Methyl-1,4,5,6-tetrahydro-5-methoxycarbonylpyrimidine 1,4,5,6-Tetrahydro-5-methoxycarbonylpyrimidine hydrochloride (300 mg, 1.35 mmol) and NaH (60% in mineral oil 107 mg, 1.35 mmol) were suspended in anhydrous DMF (5 ml) in an oven dried round bottom flask with stirring under nitrogen. After stirring 15 minutes $CH_3I$ 84µl, 1.35 mmol) was added via syringe and stirring continued 3 hours at room temperature. The solvents were evaporated in vacuo and the residue triturated with chloroform. The resulting suspension was filtered and evaporated in vacuo. Chromatography (silica, chloroform/methanol, 9:1) gave 160 mg (76%) crystals mp 93°–95° C. identified by 300 MHz nmr; ms m/z=156.

Example 8

1-Methyl-1,4,5,6-Tetrahydro-5-(3-methyl-1,2,4-oxadiazol-5-yl)pyrimidine

Sodium hydride (60% dispersion in mineral oil 112 mg, 2.8 mmol) and acetamidoxime (207 mg, 2.8 mmol) are suspended in dry THF (16 ml) in an oven dried round bottom flask under nitrogen with stirring at 0° C. After 10 minutes the grey suspension is refluxed for 30 minutes giving a white suspension. 1-Methyl-1,4,5,6-tetrahydro-5-methoxycarbonylpyrimidine (593 mg, 2.8 mmol) dissolved in dry THF (4 ml) and anhydrous ethanol (1 ml) is added via syringe and reflux continued 15 hours. The suspension is evaporated in vacuo to a yellow gum and chromatographed (silica, chloroform/methanol, 9:1) to yield 24 mg (rf=0.07, 4%) solids identified by 300 MHz nmr and ms m/z=180.

Example 9

1-Triphenylmethyl-1,4,5,6-tetrahydro-5-methoxycarbonylpyrimidine 1,4,5,6-Tetrahydro-5-methoxycarbonylpyrimidine hydrochloride (1.49 g, 8.3 mmol), 1,8 diazabicyclo[5.4.0] undec-7ene, (hereinafter diazabicycloundecene and/or DBU), (2.5 mL, 16.6 mmol), and tritylchloride (2.32 g, 8.3 mmol) were suspended in anhydrous DMF (20 ml) with stirring under nitrogen at room temperature. After 18 hours stirring the suspension was evaporated in vacuo and the residue chromatographed (silica, chloroform/methanol, 9:1) to yield 2.28 g (rf=0.15, 71%) white crystalline solid identified by 300 MHz nmr and ms m/z=384.

1-Triphenylmethyl-1,4,5,6-tetrahydro-5-(3-methyl-1,2,4-oxadiazol-5-yl)pyrimidine Sodium hydride (60% dispersion in mineral oil 26 mg, 0.65 mmol) and acetamidoxime (48 mg, 0.65 mmol) were suspended in dry THF (4 ml) in an oven dried round bottom flask with stirring under nitrogen at 0° C. After 15 minutes stirring the ice bath was removed and the grey suspension refluxed 45 minutes to give a white suspension. 1-Triphenylmethyl-1,4,5,6-tetrahydro-5-methoxycarbonylpyrimidine (250 mg, 0.65 mmol) was added dissolved in dry THF (3 ml) and reflux continued 18 hours. The solvents were evaporated in vacuo and the residue taken up in water (10 ml). The aqueous suspension was extracted exhaustively with chloroform and the organics dried over $MgSO_4$. After evaporation the organic residue was chromatographed (silica, chloroform/methanol, 9:1) to yield 93 mg (rf=0.26, 35%) white crystals, mp 72°–74° C. identified by 300 MHz nmr and ms m/z=408. Calculated: C 76.44, H 5.9, N 13.7; found: C 76.27, H 6.06, N 13.59.

1,4,5,6-Tetrahydro-5-(3-methyl-1,2,4-oxadiazol-5-yl)pyrimidine trifluoroacetate

1-Triphenylmethyl-1,4,5,6-tetrahydro-5-(3-methyl-1,2,4-oxadiazol-5-yl)pyrimidine (254 mg, 0.6 mmol) is dissolved in trifluoroacetic acid (TFA) (1 mL) with stirring at room temperature for 24 hours. The dark solution is then evaporated in vacuo, and the residue recrystallized from methanol/ether to yield 105 mg (62%) white crystals, mp 120°–122° C. identified by 300 MHz nmr. Calculated: C 38.57, H 3.96, N 19.99; found: C 38.72, H 4.09, N 19.78.

Example 10

5-Acetoxy-1,4,5,6-tetrahydropyrimidine HCl

5-Hydroxy-1,4,5,6-tetrahydropyrimidine (JOC, 1966, 31, 3838; 1 g, 10 mmol) was dissolved in glacial acetic acid (25 ml) with stirring, and thionylchloride (0.73 ml, 10 mmol) was added dropwise. The resulting solution was refluxed 19 hours, then evaporated to dryness in vacuo. The residue was taken up in water (5 ml), the pH adjusted to 12 (sat. $Na_2CO_3$), and extracted with chloroform. The chloroform was dried ($MgSO_4$) and evaporated in vacuo to 440 mg (25%) product as a clear oil identified by 400 MHz nmr. The oil was converted to its HCl salt in anhydrous ethanol with addition of IM HCl in ether. After evaporation of solvents the resulting crude HCl salt was recrystallized from ethanol to yield 128 mg (7%) white crystals, mp 287°–289° C. 400 MHz nmr and ir confirmed product.

Calculated: C 40.34, H 6.2, N 15.69; found: C 40.45, H 6.19, N 15.53.

Example 11

1-Methyl-5-methoxycarbonylpyrimidinium iodide

5-Methoxycarbonylpyrimidine (597 mg, 4.3 mmol) and methyliodide (1.6 ml, 26 mmol) were dissolved in acetonitrile (20 ml) in a stoppered flask and stirred at room temperature. After five days diethyl ether was added to precipitate red crystalline product 314 mg (26%), mp 167°–170° C. with effervescence. Calculated: C 30.02, H 3.24, N 10.00; found: C 29.88, H 3.30, N 10.07.

1-Methyl-5-methoxycarbonyl-1,2,3,6-tetrahydropyrimidine HCl

1-Methyl-5-methoxycarbonylpyrimidinium iodide (2.8 g, 7.2 mmol) was dissolved in anhydrous methanol (50 ml) and NaBH$_4$ (270 mg, 7.2 mmol) was added at room temperature with stirring. After stirring overnight the solvents were removed in vacuo. The residue was taken up in water (50 ml), extracted with chloroform and the extracts dried (MgSO$_4$). The residue obtained on removal of solvents was chromatographed (silica, chloroform/methanol, 9:1) to give the product as a yellow resin rf=0.35 185 mg (16%) identified by 400 MHz nmr. The hydrochloride salt was obtained by addition of 1M HCl in ether to an ethanol solution of the resin, evaporation of solvents and recrystallization (ethanol/ether) to yield 35 mg (15%) yellow crystals mp 160°–162° C.. Calculated: C 43.64, H 6.80, N 14.54; found: C 43.55, H 6.65, N 14.40.

Example 12

5-(1,3-dioxolan-2-yl)pyrimidine

Pyrimidine-5-carboxaldehyde (1.017 g, 9.41 mmol) was dissolved in benzene (25 ml) with heat in a 100 ml round bottomed flask fitted with a condenser, drying tube and a Dean-stark trap. p-Toluene sulfonic acid (0.179 g, 0.941 mmol) and ethylene glycol (1.1 ml, 18.82 mmol) were added and the mixture refluxed overnight. After cooling to room temperature the excess benzene was evaporated in vacuo. Saturated sodium carbonate (10 ml) was added and extracted with chloroform (7×10 ml). The chloroform extract was dried over magnesium sulfate, filtered and the solvent evaporated in vacuo to give 1.1611 g (81%) yellow oil. TLC on silica gel using chloroform/methanol (9:1) indicated the product and some starting material. Column chromatographic separation on silica gel and the same solvent system gave 0.911 g (64%) yellow oil rf=0.78 which was freeze-dried in a lyophilizer to obtain crystals. 300 MHz nmr indicated product. Microanalysis calc.: C 55.25, H 5 30, N 18.42; found: C 55.12, H 5.22, N 18.24.

1-Methyl-5-(1,3-dioxolan-2-yl)pyrimidinium iodide 5-(1,3-dioxolan-2-yl)pyrimidine (0.573 g, 3.77 mmol) and acetonitrile (3 ml) were stirred under dry nitrogen in a bomb tube with rubber seal. Methyl iodide (0.7 ml, 11.30 mmol) was added, the bomb properly sealed and stirring continued at room temperature overnight. This resulted in a yellow suspension which was vacuum-filtered to obtain yellow powdery crystals. The powder was put in drying pistol to give 0.881 g (84%) yellow crystals Recrystallization from ethanol gave fine crystals mp 188°–190° C. 300 MHz nmr in dimethyl sulfoxide (DMSO) indicated product. Microanalysis calc: C 32.67, H 3.77, N 9.53; found: C 32.66, H 3.81, N 9.42.

1-Methyl-1,2,3,6-tetrahydro-5-(1,3-dioxolan-2-yl)pyrimidine Hydrochloride

1-Methyl-5-(1,3-dioxolan-2-yl) pyrimidinium iodide (0.881 g, 3 mmol) and NaBH$_4$ (113 mg, 3 mmol) are stirred in methanol (20 mL) under dry nitrogen in around bottom flask with a rubber septum. This results in a yellow solution which is vacuum-evaporated, taken up in water, and extracted with chloroform. The residue obtained on evaporation of the chloroform is chromatographed (silica, chloroform/methanol, 9:1) to yield the free base, which is converted to its hydrochloride salt. Recrystallization from ethanol/ether gives fine white crystals (500 mg, 80%) identified by 300 MHz nmr.

Example 13

5-(1,3-oxathiolan-2-yl)pyrimidine

Pyrimidine-5-carboxaldehyde (1 g, 9.25 mmol), p-toluene sulfonic acid (0.176 g, 0.95 mmol) and 2-mercaptoethanol (0.65 ml, 9.25 mmol) were all put in a 50 ml round bottomed flask, fitted with a condenser, drying tube and a Dean-stark trap. Toluene (30 ml) was added and the mixture refluxed with stirring overnight, cooled to room temperature and excess toluene evaporated in vacuo. Saturated sodium carbonate 10 ml was added and extracted with chloroform (7×10 ml). The extract was dried over MgSO$_4$, filtered and the solvent evaporated in vacuo to 1.73 g (115%) crude yellow oil. TLC (silica; chloroform/methanol 9.8:0.2) indicated the product and some impurities.

Column chromatographic separation on silica gel using the same solvent system gave 0.780 g (52%) yellow oil. 300 MHz nmr indicated pure compound. Microanalysis calc.: C 49.98, H 4.79, N 16.66, S 19.06; found: C 50.02, H 5.04, N 16.48, S 18.91.

1-Methyl-5-(1,3-oxathiolan-2-yl)pyrimidinium Iodide 5-(1,3-oxathiolan-2-yl)pyrimidine (0.780 g, 5.1 mmol) and acetonitrile (3 ml) are stirred under dry nitrogen in a bomb tube with rubber seal. Methyl iodide (0.7 ml, 11.30 mmol) is added, the bomb properly sealed, and stirring continued at room temperature overnight. This results in a yellow suspension which is vacuum-filtered to obtain yellow powdery crystals. The powder is put in a drying pistol to give 1.32 g (84%) yellow crystals. Recrystallization from ethanol gives fine crystals identified by 300 MHz nmr.

1-Methyl-1,2,3,6-tetrahydro-5-(1,3-oxathiolan-2-yl)pyrimidine Hydrochloride 1-Methyl-5-(1,3-dioxolan-2-yl) pyrimidinium iodide (1.32 g, 4.3 mmol) and NaBH$_4$ (161 mg, 4.3 mmol) are stirred in methanol (20 mL) under dry nitrogen in a round bottom flask fitted with a rubber septum. This results in a yellow solution which is vacuum-evaporated, taken up in water, and extracted with chloroform. The residue obtained on evaporation of the chloroform is chromatographed (silica, chloroform/methanol, 9:1) to yield the free base, which is converted to its hydrochloride salt. Recrystallization from ethanol/ether gives fine white crystals (772 mg, 80%) identified by 300 MHz nmr.

Example 14

2-Amino-5-methoxycarbonylpyridine

6-Aminonicotinic acid (1.06 g, 7.7 mmol) was suspended with stirring in anhydrous methanol (50 ml), and thionyl chloride (0.55 ml, 7.7 mmol) was added dropwise. The suspension was refluxed to a clear solution over 15 hours. The solvent was evaporated in vacuo and the residue taken up in water (20 ml). The solution was raised to pH 9 (sat. Na$_2$CO$_3$), extracted with chloroform, and dried over MgSO$_4$. Evaporation of the chloroform gave 1.23 g (100%) product as white crystals identified by 400 MHz nmr and ir 1694 cm$^{-1}$.

2-Amino-3,4,5,6-tetrahydropyridine-5-carboxylic acid HCL

2-Amino-5-methoxycarbonylpyridine (0.912 g, 6.6 mmol) was dissolved in 90% ethanol (137 ml) and conc. HCl (3.5 ml, 40 mmol) was added. The solution was hydrogenated over PtO$_2$ (200 mg) in a Parr shaker apparatus at room temperature and 29 psig for 2 hours. Filtration and evaporation gave 1.05 g (89%) crude white crystals identified as the product by 400 MHz nmr and ir 3350, 3011, 1714 cm$^{-1}$.

2-Amino-5-methoxycarbonyl-3,4,5,6-tetrahydropyridine HCl

2-Amino-3,4,5,6-tetrahydropyridine-5-carboxylic acid HCl (1 g, 5.6 mmol) was suspended in anhydrous methanol (100 ml), and thionyl chloride (0.5 ml, 7 mmol) was added dropwise with stirring at room temperature. The resulting solution was refluxed overnight and then evaporated to dryness in vacuo. The resulting crude white solid was recrystallized from methanol/ether to give white crystals 589 mg (54%) mp 177-179.C, identified as product by 300 MHz nmr and ir 1733 cm$^{-1}$. Calculated: C 43.64, H 6.8, N 14.55; found: C 43.63, H 6.75, N 14.56.

Example 15

2-Amino-3,4,5,6-Tetrahydropyridine-3-carboxylic acid HCl

2-Aminonicotinic acid (0.912 g, 6.6 mmol) was dissolved in 90% methanol (137 ml) and conc. HCl (3.5 ml, 40 mmol) was added. The solution was hydrogenated over PtO$_2$ (200 mg) in a Parr shaker apparatus at room temperature and 29 psig for 2 hours. Filtration and evaporation gave 1.22 g (100%) oily product identified by ir 3300-2500, 1724 cm$^{-1}$.

2-Amino-3-methoxycarbonyl-3,4,5,6-tetrahvdropyridine HCl

2-Amino-3,4,5,6-tetrahydropyridine-3-carboxylic acid HCl (1.2 g, 6.6 mmol) was suspended in anhydrous methanol (100 ml), and thionyl chloride (0.5 ml, 7 mmol) was added dropwise with stirring at room temperature. The resulting solution was refluxed overnight and then evaporated to dryness in vacuo. The resulting crude white solid was recrystallized from methanol/ether to give white crystals 613 mg (46%) mp 138°-139° C., identified as product by 300 MHz nmr and ir 1737 cm$^{-1}$. Calculated: C 43.64, H 6.8, N 14.55; found: C 43.75, H 6.87, N 14.57.

Example 16

2-Amino-3,4,5,6-tetrahydropyridine-4-carboxylic acid HCL

2-Aminopyridine-4-carboxylic acid (Farmaco. Ed. Sci. 1958, 13, 485; 1.38 g, 10 mmol) was dissolved in 90% methanol (210 ml) and conc. HCl(4.9 ml, 60 mmol) was added. The solution was hydrogenated over PtO$_2$ (200 mg) in a Parr shaker apparatus at room temperature and 29 psig for 2 hours. Filtration and evaporation gave 1.57 g (88%) crude white crystals identified as the product by 300 MHz nmr and ir 1728 cm$^{-1}$.

2-Amino-4-methoxycarbonyl-3,4,5,6-tetrahydropyridine HCL

2-Amino-3,4,5,6-tetrahydropyridine-4-carboxylic acid HCl (1.54 g, 8.6 mmol) was suspended in anhydrous methanol (100 ml), and thionyl chloride (0.6 ml, 8.6 mmol) was added dropwise with stirring at room temperature. The resulting solution was refluxed overnight and then evaporated to dryness in vacuo. The resulting crude white solid was recrystallized from methanol/ether to give white crystals 452 mg (27%) mp 180°-181° C., identified as product by 300 MHz nmr and ir 1733 cm$^{-1}$. Calculated: C 43.64, H 6.8, N 14.55; found: C 43.42, H 6.65, N 14.66.

Example 17

2-Amino-3,4,5,6-tetrahydropyridine-6-carboxylic acid HCl

2-Aminopyridine-6-carboxylic acid (Farmaco. Ed. Sci. 1959, 14, 594; 2.01 g, 14.5 mmol) was dissolved in 90% methanol (200 ml) and conc. HCl (7.2 ml, 87.4 mmol) was added. The solution was hydrogenated over PtO$_2$ (340 mg) in a Parr shaker apparatus at room temperature and 29 psig for 2 hours. Filtration and evaporation gave 2.08 g (80%) crude white crystals identified as the product by 300 MHz nmr and ir 1724 cm$^{-1}$.

2-Amino-6-methoxycarbonyl-3,4,5,6-tetrahydropyridine HCL

2-Amino-3,4,5,6-tetrahydropyridine-6-carboxylic acid HCl (1.99 g, 11.1 mmol) was suspended in anhydrous methanol (100 ml), and thionyl chloride (0.8 ml, 11.1mmol) was added dropwise with stirring at room temperature. The resulting solution was refluxed overnight and then evaporated to dryness in vacuo. The resulting crude white solid was recrystallized from ethanol to give white crystals 656 mg (31%) mp 132°-134° C., identified as product by 300 MHz nmr and ir 1753 cm$^{-1}$. Calculated: C 43.64, H 6.8, N 14.55; found: C 43.80, H 6.81, N 14.46.

Example 18

2-Trifluoromethyl-5-hvdroxy-1,4,5,6-tetrahyvdropyrimidine 1,3-Diamino-2-hydroxypropane (10 g, 111 mmol) and ethyltrifluoroacetate (13.5 ml, 114 mmol) were dissolved in xylene (85 ml) and refluxed overnight in a Dean-Stark apparatus. The solvents were evaporated in vacuo to give a dark viscous oil 21 g identified by 300 MHz nmr as product.

5-Acetoxy-2-trifluoromethyl-1,4,5,6-tetrahydropyrimidine HCl

2-Trifluoromethyl-5-hydroxy-1,4,5,6-tetrahydropyrimidine (111mmol) was dissolved in glacial acetic acid (100 ml) with stirring, and thionyl chloride (8.1 ml, 111 mmol) was added dropwise. The resulting solution was refluxed 19 hours, then evaporated to dryness in vacuo. The residue was taken up in water (50 ml), the pH adjusted to 9 (sat. Na$_2$CO$_3$), and extracted with chloroform. The chloroform was dried (MgSO$_4$) and evaporated in vacuo to 2 g (90%) crude product as a clear red oil identified by 400 MHz nmr. The oil was converted to its HCl salt in anhydrous ethanol with addition of 1M HCl in ether. Unreacted starting material, as the hydrochloride, was collected and the mother liquor evaporated, treated with aqueous base and extracted with chloroform again. Chromatography (silica 60, chloroform/methanol) gave 440 mg crude product as an oil that was again converted to its hydrochloride salt in ethanol. After evaporation of solvents the crude HCl salt was recrystallized from ethanol/ether to yield 242 mg (0.8%) tan crystals, mp 197°–199° C. 400 MHz nmr confirmed the product calculated: C 34.09, H 4.09, N 11.36; found: C 34.13, H 4.14, N 11.50.

Example 19

2-methyl-5 acetoxy-1,4,5,6-tetrahydropyrimidine

2-Methyl-5-hydroxy-1,4,5,6-tetrahydropyrimidine (JOC 1966, 31, 3838; 1.5 g, 13.3 mmol) was dissolved in glacial acetic acid (100 ml) with stirring, and thionyl chloride (1 ml, 13.1 mmol) was added dropwise. The resulting solution was refluxed 19 hours, then evaporated to dryness in vacuo. The residue was taken up in water (5 ml), the pH adjusted to 9 (sat. $Na_2CO_3$), extracted with chloroform and the organics discarded. The aqueous layer was then adjusted to pH 12 (sat. NaOH) and extracted with chloroform. The chloroform was dried ($MgSO_4$) and evaporated in vacuo to 575 mg (28%) white crystals, mp 141°–146° C. 400 MHz nmr confirmed the product calculated: C 53.82, H 7.75, N 17.94; found: C 53.9, H 7.73, N 17.77.

Example 20

1-Methyl-3-triphenylmethyl-5(3-methyl-1,2,4-oxadiazol-5-yl)-1,4,5,6-tetrahydropyrimidinium Iodide Methyliodide (38 $\mu$l, 0.6 mmol) was added to a stirred solution of 1-triphenylmethyl-5(3-methyl-1,2,4-oxadiazol-5-yl)-1,4,5,6-tetrahydropyrimidine (250 mg, 0.6 mmol) in chloroform (1ml), in a round bottom flask with a septum, at room temperature. After 12 hours stirring the solvents were evaporated in vacuo giving 330 mg (100%) crude white crystals identified by 300 MHz nmr.

1-Methyl-5(3-methyl-1,2,4-oxadiazol-5-yl)-1,4,5,6-tetrahydropyrimidine HCl

1-Methyl-3-triphenylmethyl-5(3-methyl-1,2,4-oxadiazol-5-yl)-1,4,5,6-tetrahydropyrimidinium Iodide (330 mg, 0.6 mmol) was dissolved in TFA (1 mL) with stirring in a stoppered round bottom flask at room temperature. After 18 hours stirring the excess TFA was evaporated in vacuo, and the dark residue triturated with ether. The ether was decanted leaving an oily residue that was taken up in ice cold sat. $Na_2CO_3$ and then extracted with chloroform. After drying and evaporation the chloroform fraction gave the free base which was converted to its HCl salt and recrystallized (methanol/ether) to yellow crystals 15 mg (12%) identified by 300 MHz nmr and ms m/z=180.

Example 21

1-Methyl-3-triphenylmethyl-5-methoxycarbonyl-1,4,5,6-tetrahydropyrimidinium iodide Methyliodide (47 $\mu$l, 0.6 mmol) is added to a stirred solution of 1-triphenylmethyl-5-methoxycarbonyl-1,4,5,6-tetrahydropyrimidine (288 mg, 0.75 mmol) in chloroform (5 ml), in a round bottom flask with a septum, at room temperature. After 12 hours stirring the solvents are evaporated in vacuo giving 395 mg (100%) white crystals identified by 300 MHz nmr.

1-Methyl-5-methoxycarbonyl-1,4,5,6-tetrahydropyrimidine

1-Methyl-3-triphenylmethyl-5-methoxycarbonyl-1,4,5,6-tetrahydropyrimidinium iodide (395 mg, 0.75 mmol) is dissolved in TFA (1 ml) with stirring in a stoppered round bottom flask at room temperature. After 18 hours stirring the excess TFA is evaporated in vacuo, and the dark residue triturated with ether. The ether is decanted leaving an oily residue that is taken up in ice cold sat. $Na_2CO_3$ and then extracted with chloroform. After drying and evaporation the chloroform fraction gave the free base which is recrystallized (chloroform/hexane) to yellow crystals 88 mg (74%) identified by 300 MHz nmr, ms m/z=156.

Example 22

Amino(pyrimidin-5-yl)acetonitrile

Potassium cyanide (651 mg, 10 mmol) and ammonium chloride (588 mg, 11 mmol) are dissolved in water (2.6 mL) with stirring. Pyrimidine-5-carboxaldehyde (1.08 g, 10 mmol) in methanol (2.6 mL) is added to the clear solution rapidly, giving first a yellow, then a dark red solution, and mildly exothermic reaction. The water is evaporated after three hours stirring, and the reddish residue is chromatographed (silica, chloroform/methanol) to give a yellow solid 1.1 g (82%) identified as product ms m/z=134.

Amino(pyrimidin-5-yl)acetamide

Amino(pyrimidin-5-yl)acetonitrile (1.1 g, 8.2 mmol) is hydrolyzed by refluxing in a small volume of dilute HCl for 1 hour. The pH is raised to 10 by addition of saturated sodium carbonate and the mixture then extracted with chloroform. Evaporation of the chloroform and chromatography (silica, chloroform/methanol) gives product as a yellow solid 950 mg (81%) ms m/z=142.

Amino(1,4,5,6-tetrahydropyrimidine-5-yl)acetamide dihydrochloride

Amino(pyrimidin-5-yl)acetamide (950 mg, 6.7 mmol) is suspended in a mixture of 50 ml water and concentrated hydrochloric acid (13.3 mmol). The mixture is hydrogenated at 26 psig over 300 mg Pd-on-carbon 10% in a Parr hydrogenator for 3 h. Then the suspension is filtered and the filter rinsed twice with hot water (20 ml). The filtrate can be evaorated in vacuo to give 1.41 g yellow oil (92%). The oil is crystallized from anhydrous methanol/THF to give 1.33 g (87%) white crystals, identified by 300 MHz nmr.

Amino(1-triphenylmethyl-1,4,5,6-tetrahydropyrimidin-5-yl)acetamide

Amino(1,4,5,6-tetrahydropyrimidine-5-yl)acetamide dihydrochloride (1.33 g, 5.8 mmol), diazabicycloundecene (DBU, 2.6 ml, 17.4 mmol), and tritylchloride (1.61 g, 5.8 mmol) are dissolved in anhydrous DMF (20 ml) with stirring under nitrogen at room temperature. After 18 hours stirring the suspension is evaporated in vacuo, and the residue chromatographed (silica, chloroform/methanol, 9:1) to yield 1.64 g (71%) white crystalline solid, identified by 300 MHz nmr and ms m/z=398.

1-Triphenylmethyl-5(3-hydroxy-1,2,5-thiadiazol-4-yl)-1,4,5,6-tetrahydropyrimidine N-Thionylaniline (2.6 mL, 23.2 mmol) is added to amino(1-triphenylmethyl-1,4,5,6-tetrahydropyrimidin-5-yl)acetamide (1.64 g, 4.1 mmol) suspended in pyridine (25 ml). After heating at 90° C. for 48 hours the pyridine is evaporated, and the black residue partitioned between chloroform and water. The aqueous layer is lowered to pH 5 (HCl) and chromatographed (Dowex-50 W, 0.5 N ammonium hydroxide) to yield the product as a brown solid 1.05 g (61%) that can be further purified by chromatography (silica, methanol) and converted to a white crystalline hydrochloride salt, ms m/z=426.

1-Triphenylmethyl-5(3(1-n-heptanoxy)-1,2,5-thiadiazol-4-yl)-1,4,5,6-tetrahydropyrimidine HCl 1-Triphenylmethyl-5(3-hydroxy-1,2,5-thiadiazol-4-yl)-1,4,5,6-tetrahydropyrimidine (1.05 g, 2.46 mmol) and NaH (60 mg, 2.46 mmol) are suspended in DMF (20 ml), and 1-iodoheptane (0.4 ml, 2.46 mmol) is added via syringe at room temperature. After stirring 5 minutes the reaction can be heated to 60° C. for 18 hours. DMF is then evaporated in vacuo, the residue dissolved in chloroform, and washed with water and saturated brine. Evaporation of the chloroform and chromatography (silica, chloroform/methanol) gives the free base which is converted to its hydrochloride salt 580 mg (42%) ms m/z=526.

5(3(1-n-heptanoxy)-1,2,5-thiadiazol-4-yl)-1,4,5,6-tetrahydropyrimidine Trifluoroacetate 1-Triphenylmethyl-5(3(1-n-heptanoxy)-1,2,5-thiadiazol-4-yl)-1,4,5,6-tetrahydropyrimidine HCl (580 mg, 1 mmol) is dissolved in TFA (11 ml) and stirred overnight at room temperature. The TFA is evaporated and the resulting dark oil triturated with ether. After decanting the ether, the remaining solids are recrystallized from methanol/ether to give 344 mg (87%) white crystals identified by 300 MHz nmr, ms m/z=360.

Example 23

1,4,5,6-Tetrahydro-5-(3-ethyl-1,2,4-oxadiazol-5-yl)pyrimidine trifluoroacetate Prepared by a procedure similar to Example 9, where sodium hydride (60% dispersion in mineral oil 56 mg, 1.4 mmol) and propionamidoxime (123 mg, 1.4 mmol) were suspended in dry THF in an oven dried round bottom flask with stirring under nitrogen at 0° C. After 15 minutes stirring the ice bath was removed and the grey suspension refluxed 45 minutes to give a white suspension. 1-Triphenylmethyl-1,4,5,6-tetrahydro-5-methoxycarbonylpyrimidine (540 mg, 1.4 mmol) was added, dissolved in dry THF and reflux continued 18 hours. The solvents were evaporated in vacno and the residue was chromatographed (silica, chloroform/methanol 9:1) to yield 1-triphenylmethyl-1,4,5,6-tetrahydro-5-(3-ethyl-1,2,4-oxadiazol-5-yl)pyrimidine 420 mg (70%). This product was dissolved in triflouroacetic acid (2 mL), with stirring at room temperature for 24 hours. The yellow solution was then evaporated in vacuo, and the residue recrystallized from methanol/ether to yield 144 mg (49%) white crystals, mp 116°–118° C. identified by 300 MHz nmr.

Example 24

1,4,5,6-Tetrahydro-5-(3-n-propyl-1,2,4-oxadiazol-5-yl)pyrimidine trifluoroacetate Prepared by a procedure similar to Example 9, where sodium hydride (60% dispersion in mineral oil 108 mg, 2.7 mmol) and butyramidoxime (276 mg, 2.7 mmol) were suspended in dry THF in an oven dried round bottom flask with stirring under nitrogen at 0° C. After 15 minutes stirring the ice bath was removed and the grey suspension refluxed 45 minutes to give a white suspension. 1-Triphenylmethyl-1,4,5,6-tetrahydro-5-methoxycarbonylpyrimidine (1.04 g, 2.7 mmol) was added, dissolved in dry THF and reflux continued 18 hours. The solvents were evaporated in vacuo and the residue was chromatographed (silica, chloroform/methanol, 9:1) to yield 1-triphenylmethyl-1,4,5,6-tetrahydro-5-(3-n-propyl-1,2,4-oxadiazol-5-yl)pyrimidine 785 mg (67%). This product was dissolved in triflouroacetic acid (2 ml), with stirring at room temperature for 24 hours. The yellow solution was then evaporated in vacuo, and the residue recrystallized from methanol/ether to yield 240 mg (43%) white crystals, mp 126–128° C. identified by 300 MHz nmr.

Example 25

1,4,5,6-Tetrahydro-5-(3-n-heptyl-1,2,4-oxadiazol-5-yl)pyrimidine trifluoroacetate Prepared by a procedure similar to Example 9, where sodium hydride (60% dispersion in mineral oil 96 mg, 2.4 mmol) and n-octylamidoxime (380 mg, 2.4 mmol) were suspended in dry THF in an oven dried round bottom flask with stirring under nitrogen at 0° C. After 15 minutes stirring the ice bath was removed and the grey suspension refluxed 45 minutes to give a white suspension. 1-Triphenylmethyl-1,4,5,6-tetrahydro-5-methoxycarbonylpyrimidine (910 mg, 2.4 mmol) was added, dissolved in dry THF and reflux continued 18 hours. The solvents were evaporated in vacuo and the residue was chromatographed (silica, chloroform/methanol, 9:1) to yield 1-triphenylmethyl-1,4,5,6-tetrahydro-5-(3-n-heptyl-1,2,4-oxadiazol-5-yl)pyrimidine 810 mg (69%). This product was dissolved in triflouroacetic acid (2 mL), with stirring at room temperature for 24 hours. The yellow solution was then evaporated in vacuo, and the residue recrystallized from methanol/ether to yield 285 mg (49%) white crystals, mp 101°–102° C. identified by 300 MHz nmr.

Example 26

1,4,5,6-Tetrahydro-5-(3-n-butyl-1,2,4-oxadiazol-5-yl)pyrimidine trifluoroacetate Prepared by a procedure similar to Example 9, where sodium hydride (95% 40 mg, 1.7 mmol) and valerylamidoxime (193 mg, 1.7 mmol) were suspended in dry THF in an oven dried round bottom flask with stirring under nitrogen at 0° C. After 15 minutes stirring the ice bath was removed and the grey suspension refluxed 45 minutes to give a white suspension. 1-Triphenylmethyl-1,4,5,6-tetrahydro-5-methoxycarbonylpyrimidine (640 mg, 1.7 mmol) was added, dissolved in dry THF and reflux continued 18 hours. The solvents were evaporated in vacuo and the residue was chromatographed (silica, chloroform/methanol, 9:1) to yield 1-triphenylmethyl-1,4,5,6-tetrahydro-5-(3-n-butyl-1,2,4-oxadiazol-5-yl)pyrimidine. This product was dissolved in triflouroacetic acid (2 mL), with stirring at room temperature for 24 hours. The yellow solution was then evaporated in vacuo, and the residue recrystallized from methanol/ether to yield 150 mg (27%) white crystals, mp 98°–100° C. identified by 300 MHz nmr.

Example 27

1,4,5,6-Tetrahydro-5-(3-n-pentyl-1,2,4-oxadiazol-5-yl)pyrimidine trifluoroacetate Prepared by a procedure similar to Example 9, where sodium hydride (95% 40 mg, 1.7 mmol) and n-hexanamidoxime (217 mg, 1.7 mmol) were suspended in dry THF in an oven dried round bottom flask with stirring under nitrogen at 0° C. After 15 minutes stirring the ice bath was removed and the grey suspension refluxed 45 minutes to give a white suspension. 1-Triphenylmethyl- 1,4,5,6-tetrahydro-5-methoxycarbonylpyrimidine (640 mg, 1.7 mmol) was added, dissolved in dry THF and reflux continued 18 hours. The solvents were evaporated in vacuo and the residue was chromatographed (silica, chloroform/methanol, 9:1) to yield 1-triphenylmethyl-1,4,5,6-tetrahydro-5-(3-n-pentyl-1,2,4-oxadiazol-5-yl)pyrimidine. This product was dissolved in triflouroacetic acid (2 mL), with stirring at room temperature for 24 hours. The yellow solution was then evaporated in vacuo, and the residue recrystallized from methanol/ether to yield 110 mg (19%) white crystals, mp 97°-99° C. identified by 300 MHz nmr.

Example 28

1,4,5,6-Tetrahydro-5-(3-n-octyl-1,2,4-oxadiazol-5-yl)pyrimidine trifluoroacetate Prepared by a procedure similar to Example 9, where sodium hydride (60% dispersion in mineral oil 104 mg, 2.6 mmol) and n-nonanamidoxime (448 mg, 2.6 mmol) were suspended in dry THF in an oven dried round bottom flask with stirring under nitrogen at 0° C. After 15 minutes stirring the ice bath was removed and the grey suspension refluxed 45 minutes to give a white suspension. 1-Triphenylmethyl-1,4,5,6-tetrahydro-5-methoxycarbonylpyrimidine (1.0 g, 2.6 mmol) was added dissolved in dry THF and reflux continued 18 hours. The solvents were evaporated in vacuo and the residue was chromatographed (silica, chloroform/methanol, 9:1) to yield 1-triphenylmethyl-1,4,5,6-tetrahydro-5-(3-octyl-1,2,4-oxadiazol-5-yl)pyrimidine 780 mg (60%). This product was dissolved in triflouroacetic acid (2 ml), with stirring at room temperature for 24 hours. The yellow solution was then evaporated in vacuo, and the residue recrystallized from methanol/ether to yield 182 mg (30%) white crystals, mp 97°-99° C. identified by 300 MHz nmr.

The biological activity of representative compounds of the present invention was demonstrated using a number of tests. These tests included using $^3$H-1-quinuclidinyl benzilate (QNB), $^3$H-pirenzepine (PZ), $^3$H-oxotremorine M (OXO-M) to evaluate the effectiveness of the compounds for binding to muscarinic receptors. The potency and efficacy of the compounds and their salts as selective $M_1$ agonists were evaluated by measuring phosphoinositide (PI) turnover in the cortex, PI turnover in the hippocampus. Further details of the testing methods are set forth immediately below.

Binding to Muscarinic Receptors

Binding was carried out essentially as described previously [Farrar, J.R. Hoss, W., Herndon, R.M. and Kuzmiak, M. Characterization of Muscarinic Cholinergic Receptors in the Brains of Copper-Deficient Rats, J. Neurosci 5:1083-1089, 1985.] Binding was determined indirectly by the ability of compounds to compete with 50 pM [$^3$H]-1-quinuclidinyl benzilate ([$^3$H]-QNB) in a suspension of brain membranes. Each sample contained approximately 10 pM receptors (2–4 μg/ml of protein) in 40 mM sodium/potassium phosphate buffer, pH 7.4 and varying concentrations of compound in a final volume of 10 ml. Samples were incubated for 2.0 hr. at room temperature and then filtered through glass fiber filters using a Brandell cell harvester adapted for receptor binding work and the filters washed twice with two 5-ml portions of cold buffer. Nonspecific binding was evaluated by the inclusion of excess atropine in a separate set of samples. IC$_{50}$ values were determined from Hill plots of the inhibition data and are reported as means of three independent experiments each performed in triplicate.

Other binding was determined indirectly by the ability of compounds to compete with 1 nM $^3$H-pirenzepine ($^3$H—PZ), or 3 nM $^3$H-oxotremorine M ($^3$H—OXO—M) in a suspension of brain membranes. Each sample contained approximately 0.1 mg/ml protein for $^3$H—OXO—M in 20 mM Tris-Cl buffer with 1 mM MnCl$_2$ and varying concentrations of compound in a final volume of 10 ml. Samples were incubated 1 hr. for $^3$H—PZ, and 15 minutes for $^3$H—OXO—M at room temperature and then filtered through glass fiber filters using a Brandell cell harvester adapted for receptor binding work and the filters were washed twice with two 5-ml portions of cold buffer. Nonspecific binding was evaluated by the inclusion of excess atropine in a separate set of samples. IC$_{50}$ values were determined from Hill plots of the inhibition data and are reported as means of three independent experiments each performed in triplicate.

Preparation of Brain Membranes

Rats were killed by cervical dislocation and their brains rapidly removed. Tissue was homogenized in 9 vol. (w/v) of a 40 mM sodium-potassium phosphate buffer solution (pH 7.4) buffer solution with a Brinkman Polytron homogenizer five times for 10 sec at 5 sec intervals. The crude homogenate was subjected to centrifugation for 10 min at 1000×g, the supernatant saved, and the pellet resuspended in 9 vol. (w/v) of homogenization buffer and spun for another 10 min at 1000×g. The supernatants were combined and spun again for 30 min at 17,500×g. The resultant pellet was resuspended by homogenization in a Teflon-glass homogenizer in 10 vol. of buffer, and washed by centrifugation at 17,500×g for 30 min. The final pellet was resuspended by hand homogenization with a Teflon and glass homogenizer in buffer. The suspension was then divided into several portions and stored at −70° C.

Tissue Preparation

Male Long Evans rats (200–300 g) were decapitated and their brains were rapidly removed and dissected according to the method of Glowinski and Iversen. [Glowinski, J. and Iversen, L.L., Regional Studies of Catecholamines in Rat Brain I: The Disposition of [$^3$H]norepinephrine, [$^3$H]dopamine and [$^3$H]Dopa in Various Regions of the Brain, J. Neurochem, 13:655-669, 1966.] Brain slices (300×300 μm) were prepared using a McIlwain tissue chopper and dispersed in Krebs-Hensleit buffer (KHB) containing 118 mM NaCl, 4.7 mM KCl, 1.3 mM CaCl$_2$, 1.2 mM KH$_2$PO$_4$, 1.2 mM MgSO$_4$, 25 mM NaHCO$_3$, and 11.7 mM glucose equilibrated with 95% O$_2$/5% CO$_2$ to final pH of 7.4. The slices were gently agitated at 37° C. in a shaking water bath for 45 min with three changes to buffer.

Incorporation of $^3$H1-Inositol and Agonist Stimulation of Inositol Phosphate IP Formation Immediately before each experiment, [$^3$H] inositol was purified by drying under N$_2$ and passing a portion through a 1-ml column of Dowex AG1-X8 (formate form) to remove contaminants. The continuous labeling paradigm essentially of Brown et al. (Brown, E. and Kendall, D. A. and Nahorski, S.R., Inositol Phopholipid Hydrolysis in Rat Cerbral Cortical Slices: I. Receptor Charterisation, J. Neurochem., 42: 1379-1387, 1984) was selected because of its simplicity and sensitivity. Aliquots (25 microliters) of tissue slices were pipetted into flat-bottomed Beckman-biovials (5-ml capacity) containing 0.3 mM [$^3$H]-inositol (15 Ci/mmol) and 10 mM LiCl in 245 microliters of buffer. The vials were then gassed, capped and incubated at 37° C. in a shaking water bath for 30 min. At the end of 30 min, agonist (or buffer for the determination of basal levels) was then added (30 microliters), and the incubation continued for an additional 45 min. The 45-min incubation period was selected on the basis of the time course of labeled inositol phosphates ([$^3$H]-IP's) accumulation under these conditions. The incubations were stopped by the addition of 0.94 ml of CHCl$_3$/MeOH (1:2, V/V) followed by 0.31 ml of CHCl$_3$ and 0.31 ml of H$_2$O. The samples were mixed with vigorous shaking and spun at 1000×g for 10 min to separate organic and aqueous phases. Aliquots (750 microliter) of the upper aqueous phase were removed for determination of [$^3$H]-IP's. In some cases 200 ml aliquots of the organic phase were removed, dried overnight and counted in 5 ml of scintillant (Amersham) for determination of [$^3$H]-inositol incorporation into phospholipids.

Assay of [$^3$H]-Labeled Inositol Phosphates

The amount of [$^3$H]-IP's formed in the assay was determined essentially according to Wreggett and Irvine (Wreggett, K.A. and Irvine, R.F., A Rapid Separation Method for Inositol Phosphates and their Isomers, *Biochem. J.*, 245:655-660, 1987) except that the separation of inositol phosphates was carried out using an Amersham Super Separator Manifold. Briefly, AC-CELL QMA anion-exchange SEP-PAK's (Waters Associates) cartridges were converted into the formate form by washing first with 10 ml of a solution of 1.0 M-ammonium formate in 0.1 M-formic acid, followed by 20 ml of distilled water. The sample loading and solution delivery were performed by using disposable plastic syringes; an approximate flow rate of 10-15 ml/min was maintained. Total [$^3$H]-IP's were determined by the "batch" method in which 750 microliter aliquots of the aqueous phase obtained as described above was diluted to 3 ml with distilled water. The entire amount was loaded on to the ACCELL QMA anion-exchange SEP-PAK cartridge. The cartridge was then washed with 10 ml of distilled water, followed by 5 mM-disodium tetraborate. Radiolabeled IP's were then eluted with 1 ml of 0.6 M-ammonium formate/0.06 M formic acid/5 mM-disodium tetraborate (pH 4.75) and 0.50 ml of this eluate was counted in 5 ml of aqueous counting scintillant. Under these conditions, carbachol produced a 3-5-fold increase in IP's accumulation over the basal unstimulated value.

As representative of the compounds of this invention, and their pharmaceutically acceptable salts, and also some other compositions, the testing results of the following compounds, as produced in the examples above, are tabulated in Table I.

| Example | Compound Name: |
|---|---|
| 1 | 1,4,5,6-tetrahydro-5-methoxycarbonylpyrimidine HBr |
| 2 | 1,4,5,6-tetrahydro-5-ethoxycarbonylpyrimidine HCl |
| 3 | n-propyl 1,4,5,6-tetrahydropyrimidine-5-carboxylate HCl |
| 4 | isopropyl 1,4,5,6-tetrahydro-pyrimidine-5-carboxylate HCl |
| 5 | benzyl 1,4,5,6-tetrahydropyrimidine-5-carboxylate HCl |
| 10 | 5-acetoxy-1,4,5,6-tetrahydropyrimidine HCl |
| 11 | 1-methyl-5-methoxycarbonyl-1,2,3,6-tetrahydropyrimidine HCl |
| 14 | 2-amino-5-methoxycarbonyl-3,4,5,6-tetrahydropyridine HCl |
| 15 | 2-amino-3-methoxycarbonyl-3,4,5,6-tetrahydropyridine HCl |
| 16 | 2-amino-4-methoxycarbonyl-3,4,5,6-tetrahydropyridine HCl |
| 18 | 2-trifluoromethyl-5-acetoxy-1,4,5,6-tetrahydropyrimidine HCl |
| 19 | 2-methyl-5-acetoxy-1,4,5,6-tetrahydropyrimidine |
| 17 | 2-amino-6-methoxycarbonyl-3,4,5,6-tetrahydropyridine HCl |
| 6 | Propynyl 1,4,5,6-tetrahydropyrimidine-5-carboxylate HCl |
| 9 | 1,4,5,6-Tetrahydro-5-(3-methyl-1,2,4-oxadiazol-5-yl) pyrimidine trifluoroacetate |

In the table, $^3$H-QNB indicates general binding to muscarinic receptors and the lower the number, the higher is the potency. $^3$H-PZ indicates binding to muscarinic receptors and a preference for M$_1$ receptors involved in memory and cognition. The lower the number for $^3$H-PZ the higher the potencies; the same is true for $^3$H—OXO—M which indicates agonist binding. In general, the higher the ratio of the value for $^3$H—PZ to the value for $^3$H—OXO—M the better is the agonistic characteristic.

PI Cortex measures a relevant biochemical response for muscarinic receptors linked to M$_1$, M$_3$, M$_5$ receptors and activity indicates it is an agonist at M$_1$ and/or M$_3$ and/or M$_5$ receptors. Higher activity numbers indicate higher efficacy relative to carbachol, a full agonist at all muscarinic receptors.

Phosphoinositide turnover in the hippocampus indicates a biological response in an area of the brain where M$_1$ receptors predominate. Higher numbers indicate greater efficacy and selectivity at M$_1$ receptors.

TABLE I

| Example | $^3$H-QNB | $^3$H—PZ | $^3$H—OXO-M | PI Cortex |
|---|---|---|---|---|
| 1 | 9.2 | 3.9 | 0.09 | 131/100 μM |
| 2 | 1.9 | 0.73 | 0.16 | 150/100 μM |
| 3 | 2.1 | 1.33 | 1.085 | 7.1/100 μM |
| 4 | 3.5 | 2.26 | 1.76 | 7.2/100 μM |
| 5 | ~1 | 1.265 | 1.09 | 3.5/100 μM |
| 10 | 31.6 | 10 | 0.64 | |
| 11 | 25.1 | 15 | 2.4 | 182/1 mM |
| 14 | 7.3 | 0.77 | 0.114 | 265/100 μM |
| 9 | 2.0 | 0.47 | 0.026 | 700/100 μM |
| 6 | 1.9 | | | 230/100 μM |
| 15 | 83 | 13 | >10 | −5.5/100 μM |
| 16 | 130 | | | 9.0/100 μM |
| 18 | 8.7 | >10 | >10 | |
| 19 | 100 | >10 | >10 | |
| 17 | 130 | >10 | >10 | 5.9/100 μM |

Key: $^3$H-QNB, $^3$H—PZ, and $^3$H—OXO-M are IC$_{50}$ values in micromoles (μM); PI is maximal % response above baseline for a dose in the range 50 μM to 1 mM.

Phosphoinositide turnover in the hippocampus was measured on Examples 1, 9, 10, 18 and 19. The values (as the above Key indicates for PI, i.e. maximal response/dosage) were: 237/1 mM (Ex. 1); 70/100 μM (Ex. 10); 704/100 μM (Ex. 9); 0/50 μM (Ex. 18); and 0/50 μM (Ex. 19).

Interestingly, the 5-acetoxy-1,4,5,6-tetrahydropyrimidine HCl (Ex. 10) is effective at muscarinic receptors with acceptable binding data and is efficacious with respect to the PI response. In contrast, however, observe that 2-trifluoromethyl-5-acetoxy-1,4,5,6-tetrahydropyrimidine HCl (Ex. 18) has no PI response and even more significantly that 2-methyl-5-acetoxy- 1,4,5,6-tetrahydropyrimidine (Ex. 19), in addition to having virtually no PI response, shows extremely poor binding to muscarinic receptors. Thus the unpredictable nature of this technology will be readily apparent. Changing a hydrogen atom (Ex. 10) to a methyl group (Ex. 19) resulted in the production of an inactive and unacceptable composition. Further along these lines note the dramatic difference which results by simply changing the ring position of the same moiety. The compound 2-amino-5-methoxycarbonyl-3,4,5,6-tetrahydropyridine HCl (Ex. 14) has an unexpectedly superior PI response compared to the position isomers 2-amino-3-methoxycarbonyl-3,4,5,6-tetrahydropyridine HCl (Ex. 15), 2-amino-4-methoxycarbonyl-3,4,5,6-tetrahydropyridine HCl (Ex. 16), and compared to 2-amino-6-methoxycarbonyl-3,4,5,6-tetrahydropyridine (Ex. 17).

Based on the PI response data in Table I, it will be seen that propyl (Ex. 3), isopropyl (Ex. 4) and benzyl (Ex. 5) are not preferred ester forms for the 1,4,5,6-tetrahydropyrimidine-5-carboxylate compound or its salt composition.

While the above describes and exemplifies the present invention it will, of course, be apparent that modifications are possible such as, for example, using pro-drug forms of the compositions of this invention. These modifications, however, pursuant to the patent laws, including the doctrine of equivalents, do not, however, depart from the spirit and scope of the present invention.

We claim:

1. A compound having the formula (i), (ii), or (iii) below or a pharmaceutically acceptable salt thereof,

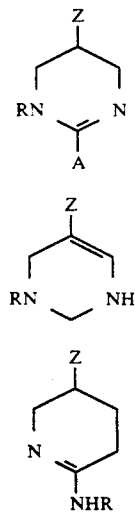

wherein A is H or NHR: R is H, alkyl of 1-7 carbon atoms, —C(O)—R' or C(O)OR'; and wherein Z is methoxycarbonyl, ethoxycarbonyl, propoxycarbonyl, acetoxy or propynyl carbonyl, and wherein R' is an alkyl group of 1-7 carbon atoms.

2. The compound or salt of claim 1 wherein said compound or salt is that of (iii).

3. The compound or salt of claim 1 wherein said compound or salt is (i) or (ii).

4. The compound or salt of claim 1 wherein said compound or salt is (i).

5. The compound or salt of claim 1 wherein said compound or salt is (ii).

6. The compound or salt of claim 1 wherein said $R^1$ radical is an alkyl group of one to two carbon atoms.

7. The compound or salt of claim 1 wherein compound or salt is that of structure (i) with the proviso that $R^1$ is not propyl, isopropyl or benzyl.

8. The compound or salt of claim 1 wherein said compound or salt is that of structure (iii) with the proviso that R is —H.

9. The compound or salt of claim 1 wherein Z is methoxycarbonyl.

10. The compound or salt of claim 1 wherein said compound or salt is of structure (ii) and wherein R is $CH_3$ and Z is $C(O)OCH_3$.

11. The compound or salt of claim 1 wherein said compound or salt is of structure (i) and wherein R is H, Z is $OC(O)CH_3$ and wherein A is H.

12. The compound or salt of claim 1 wherein said compound or salt is of structure (iii) and wherein R is H and wherein Z is $C(O)OCH_3$.

13. The compound or salt of claim 1 wherein said compound or salt is (i) and wherein A is H, R is H and Z is —$C(O)OCH_3$.

14. The compound or salt of claim 1 wherein said salt or compound is (i) and wherein Z is —$C(O)OC_2H_5$, A is H and R is H.

15. The compound of claim 1 wherein said compound or salt is (i) and wherein Z is gamma—propynyloxy carbonyl, R is H and A is H.

16. The compound or salt of claim 1 wherein said compound or salt is (i) and wherein Z is —$C(O)OCH_3$.

17. A compound as defined in claim 1 in which Z is methoxycarbonyl.

18. A substituted 1,4,5,6-tetrahydropyrimedine wherein in 2 position is not substituted or when substituted, is NHR where R is an alkyl radical of 1-7 carbon atoms and wherein the 5 position is substituted by methoxycarbonyl, ethoxycarbonyl, propoxycarbonyl, acetoxy, or propynoxycarbonyl.

19. A substituted 1,2,3,6-tetrahydropyrimidine in which the 1 position is substituted by an alkyl group of 1 or 7 carbon atoms and the 5 position is substituted by methoxy carbonyl, ethoxy carbonyl, propoxy carbonyl, acetoxy, or propynoxy carbonyl.

20. A substituted 3,4,5,6-tetrahydropyridine wherein in 2 position is substituted by NHR when R is H or an alkyl group of 1-7 atoms and the 5 position is substituted by methoxy carbonyl, ethoxy carbonyl, propoxy carbonyl, acetoxy, or propynoxy carbonyl.

21. A compound as defined in claim 1 in which R' is a branched chain alkyl group.

22. A compound or salt pharmaceutically acceptable thereof, selected from the group consisting of: 5- methoxycarbonyl-1,4,5,6-tetrahydropyrimidine; 5-acetoxy-1,4,5,6-tetrahydropyrimidine; 1-methyl-5-methoxycarbonyl-1,2,3,6-tetrahydropyrimidine; 2-amino-5-methoxycarbonyl-3,4,5,6-tetrahydropyridine; 5-ethoxycarbonyl-1,4,5,6-tetrahydropyrimidine; 5(3-methyl-1,2,4-oxadiazol-5-yl)-1,4,5,6-tetrahydropyrimidine tri-fluoroacetate; 2-amino-4-methoxycarbonyl 1,4,5,6-tetrahydropyrimidine and propynyl 1,4,5,6-tetrahydropyrimidine-5-carboxylate hydrochloride.

23. A compound or salt as defined in claim 22 that is 5-methoxycarbonyl-1,4,5,6-tetrahydropyrimidine.

24. A compound or salt as defined in claim 22 that is 5-acetoxy-1,4,5,6-tetrahydropyrimidine.

25. A compound or salt as defined in claim 22 that is 1-methyl-5-methoxycarbonyl-1,2,3,6-tetrahydropyrimidine.

26. A compound or salt as defined in claim 22 that is 2-amino-5-methoxycarbonyl-3,4,5,6-tetrahydropyridine.

27. The compound of claim 22 wherein said compound or salt is 5(3-methyl-1,2,4-oxadiazol-5-yl)-1,4,5,6-tetrahydropyrimidine tri-fluoroacetate.

28. A compounding having the formula (i), (ii), or (iii) below or a pharmaceutically acceptable salt thereof,

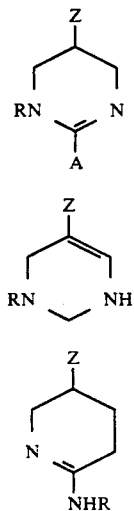

wherein A is H or NHR; R is H, alkyl of 1-7 carbon atoms, —C(O)—R¹ or C(O)OR¹; R¹ is an alkyl group of 1-7 carbon atoms; and wherein Z is methoxycarbonyl, ethoxycarbonyl, propoxycarbonyl, acetoxy, or propynoxycarbonyl.

29. In a method of providing a therapeutic benefit to a mammal comprising administering to said mammal a drug in effective amounts to stimulate a muscarinic receptor so as to provide such benefit, the improvement wherein said drug is a compound of claim 1 or its pharmaceutically salt.

30. The method of claim 29 wherein said compound is 5-methoxycarbonyl-1,4,5,6-tetrahydropyrimidine or its pharmaceutically acceptable salt.

31. The method of claim 29 wherein said compound is 5-acetoxy-1,4,5,6-tetrahydropyrimidine or its pharmaceutically acceptable salt.

32. The method of claim 29 wherein said compound is 1-methyl-5-methoxycarbonyl-1,2,3,6-tetrahydropyrimidine or its pharmaceutically acceptable salt.

33. The method of claim 29 wherein said compound is 2-amino-5-methoxycarbonyl-3,4,5,6-tetrahydropyridine or its pharmaceutically acceptable salt.

34. The method of claim 29 wherein said compound is 5-ethoxycarbonyl-1,4,5,6 -tetrahydropyrimidine or its pharmaceutically acceptable salt.

35. The method of claim 29 wherein said compound or salt is propargyl 1,4,5,6-tetrahydropyrimidine-5-carboxylate hydrochloride.

36. The method of claim 29 wherein said compound or salt is that of (iii).

37. The method of claim 29 wherein said compound or salt is that of (i) or (ii).

38. The method of claim 29 wherein said compound or salt is that of (i).

39. The method of claim 29 wherein said compound or salt is that of (ii).

40. The method of claim 29 wherein said benefit is an improved cognitive function.

41. A pharmaceutical preparation effective for stimulating a muscarinic receptor, comprising a compound of claim 1, or a pharmaceutically acceptable salt thereof, together with a pharmaceutically acceptable solid or liquid carrier.

42. The preparation of claim 41 wherein the compound or salt Z is methoxycarbonyl.

43. The preparation of claim 41 wherein said compound, or salt is at least one compound, or salt thereof, selected from the group consisting of: 5 -methoxycarbonyl-1,4,5,6-tetrahydropyrimidine; 5 -acetoxy-1,4,5,6-tetrahydropyrimidine; 1-methyl-5-methoxycarbonyl-1,2,3,6-tetrahydropyrimidine; 2-amino-5-methoxycarbonyl-3,4,5,6-tetrahydropyridine; 5-ethoxycarbonyl-1,4,5,6-tetrahydropyrimidine; 5(3-methyl-1,2,4-oxadiazol-5-yl)-1,4,5,6-tetrahydropyrimidine tri-fluoroacetate; and propyryl 1,4,5,6-tetrahydropyrimidine-5-carboxylate hydrochloride.

44. The compound, or salt, of claim 1 wherein said salt or compound is an $M_1$ muscarinic agonist.

45. The compound or salt of claim 44 wherein said compound or salt thereof is (i).

46. The compound or salt of claim 45 wherein R and A are H.

* * * * *